United States Patent
Kim et al.

(10) Patent No.: US 9,444,998 B2
(45) Date of Patent: Sep. 13, 2016

(54) METHOD FOR CONTROL OF CAMERA MODULE BASED ON PHYSIOLOGICAL SIGNAL

(71) Applicant: Samsung Electronics Co., Ltd., Gyeonggi-do (KR)

(72) Inventors: Namjin Kim, Gyeonggi-do (KR); Sora Hyun, Gyeonggi-do (KR); Hyunho Seo, Gyeonggi-do (KR); Changhyun Chun, Gyeonggi-do (KR); Yunemo Koo, Gyeonggi-do (KR); Gaeyoun Kim, Gyeonggi-do (KR); Geonsoo Kim, Gyeonggi-do (KR); Heedeog Kim, Gyeonggi-do (KR); Sunghyuk Shin, Gyeonggi-do (KR); Kihuk Lee, Gyeonggi-do (KR); Chulhwan Lee, Seoul (KR); Cheolho Cheong, Seoul (KR); Seungmin Choi, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 0 days.

(21) Appl. No.: 14/843,593

(22) Filed: Sep. 2, 2015

(65) Prior Publication Data
US 2016/0065840 A1 Mar. 3, 2016

(30) Foreign Application Priority Data
Sep. 2, 2014 (KR) .......................... 10-2014-0116510

(51) Int. Cl.
*H04N 5/232* (2006.01)
*A61B 5/00* (2006.01)
(Continued)

(52) U.S. Cl.
CPC .......... *H04N 5/23216* (2013.01); *A61B 5/024* (2013.01); *A61B 5/02416* (2013.01); *G06F 3/011* (2013.01); *H04N 5/232* (2013.01); *H04N 5/23293* (2013.01); *H04N 9/73* (2013.01)

(58) Field of Classification Search
CPC ..................... H04N 5/23216; H04N 5/23238
See application file for complete search history.

(56) References Cited

U.S. PATENT DOCUMENTS

| 5,072,248 A * | 12/1991 | Kakiuchi .............. G03B 17/38 396/263 |
| 6,885,818 B2 * | 4/2005 | Goldstein .............. G03B 17/00 351/159.03 |

(Continued)

FOREIGN PATENT DOCUMENTS

| EP | 2 617 354 | 7/2013 |
| JP | 2004-361708 | 12/2004 |

(Continued)

OTHER PUBLICATIONS

Toshiyo Tamura at al., "Wearable Photoplethysmographic Sensors—Past and Present", Electronics, ISSN 2079-9292, Apr. 23, 2014, 21 pages.

(Continued)

*Primary Examiner* — W B Perkey
(74) *Attorney, Agent, or Firm* — The Farrell Law Firm, P.C.

(57) ABSTRACT

A control method of an electronic device is disclosed. The method includes receiving an input signal including a physiological signal of a subject to be examined through a sensor module of the electronic device, detecting an input operation based on at least the input signal, and acquiring an image through a camera module according to the input operation.

29 Claims, 37 Drawing Sheets

(51) Int. Cl.
*A61B 5/024* (2006.01)
*H04N 9/73* (2006.01)
*G06F 3/01* (2006.01)

(56) References Cited

U.S. PATENT DOCUMENTS

| | | | |
|---|---|---|---|
| 6,930,707 B2 * | 8/2005 | Bates | H04N 5/232 |
| | | | 348/161 |
| 7,176,973 B2 * | 2/2007 | Takada | G06K 9/00604 |
| | | | 348/335 |
| 8,055,032 B2 * | 11/2011 | Li | G07C 9/00158 |
| | | | 382/124 |
| 2003/0021601 A1 | 1/2003 | Goldstein | |
| 2008/0253695 A1 | 10/2008 | Sano et al. | |
| 2011/0221948 A1 * | 9/2011 | Saito | G06F 3/0488 |
| | | | 348/333.01 |
| 2014/0126044 A1 | 5/2014 | Steurer | |
| 2014/0160432 A1 | 6/2014 | Brown, Jr. et al. | |
| 2014/0168406 A1 | 6/2014 | Olsson et al. | |
| 2014/0171758 A1 | 6/2014 | Ayanruoh | |
| 2014/0232885 A1 | 8/2014 | Slater et al. | |

FOREIGN PATENT DOCUMENTS

| | | |
|---|---|---|
| KR | 10-0591239 | 6/2006 |
| KR | 10-2012-0002258 | 1/2012 |
| KR | 10-2013-0088613 | 8/2013 |

OTHER PUBLICATIONS

European Search Report dated Feb. 2, 2016 issued in counterpart application No. 15183425.6-1903, 13 pages.

* cited by examiner

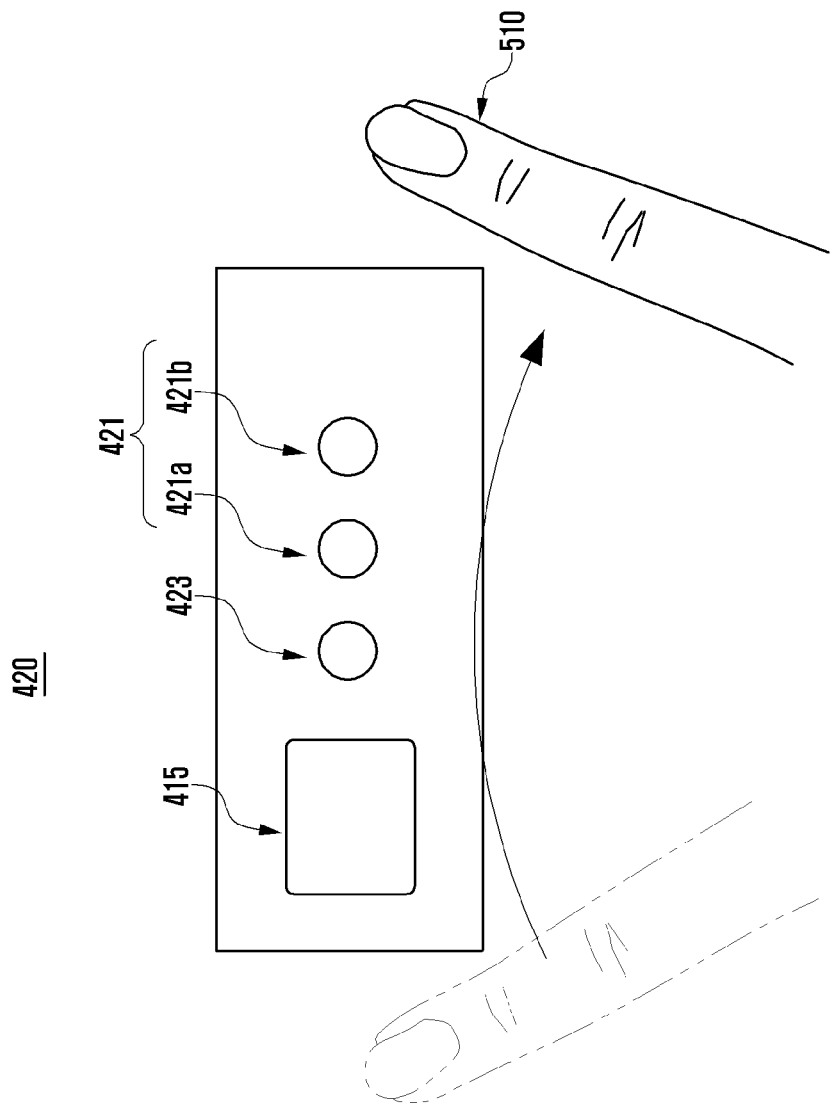

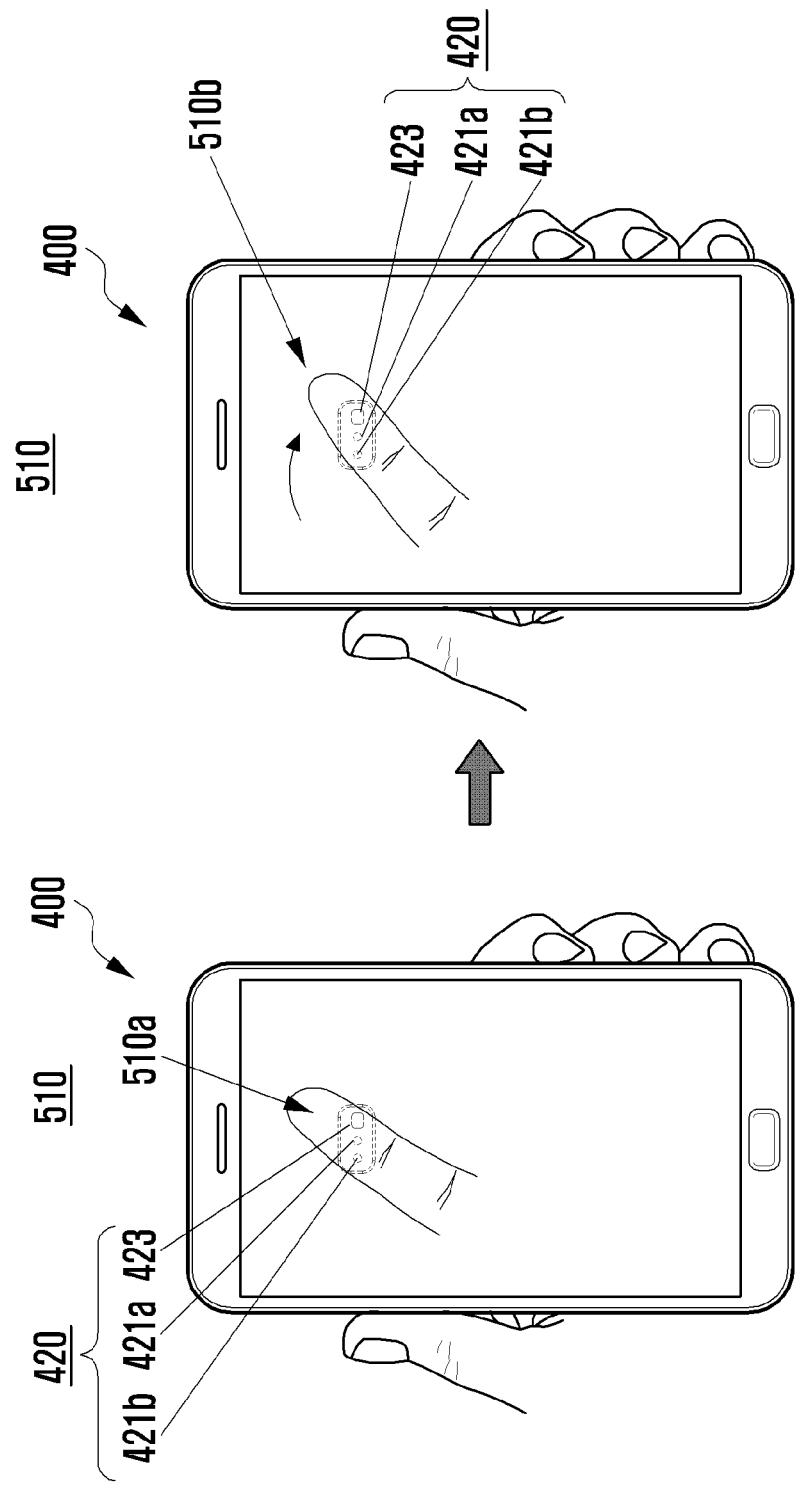

FIG. 27A
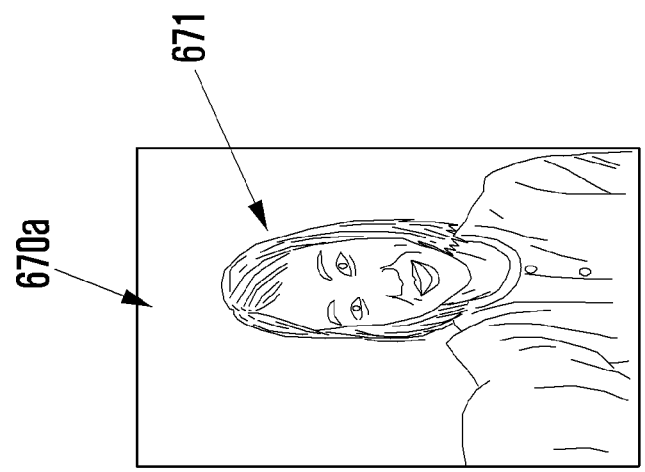
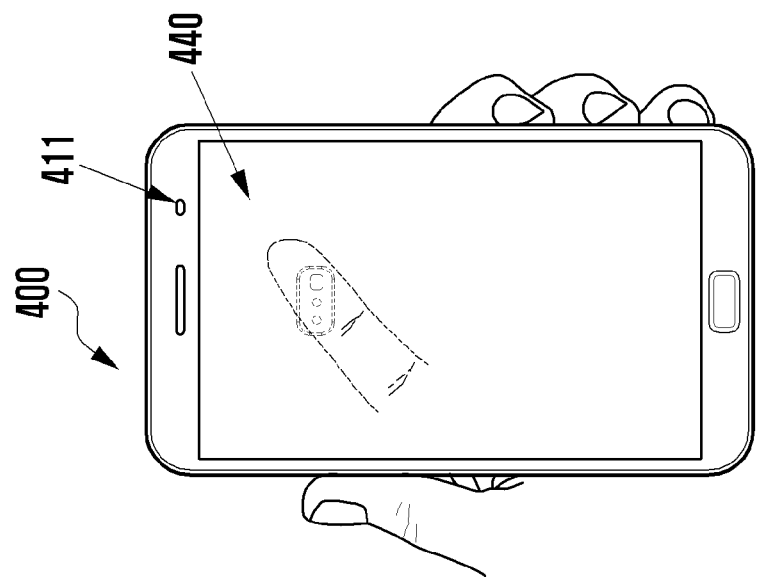

FIG. 27C
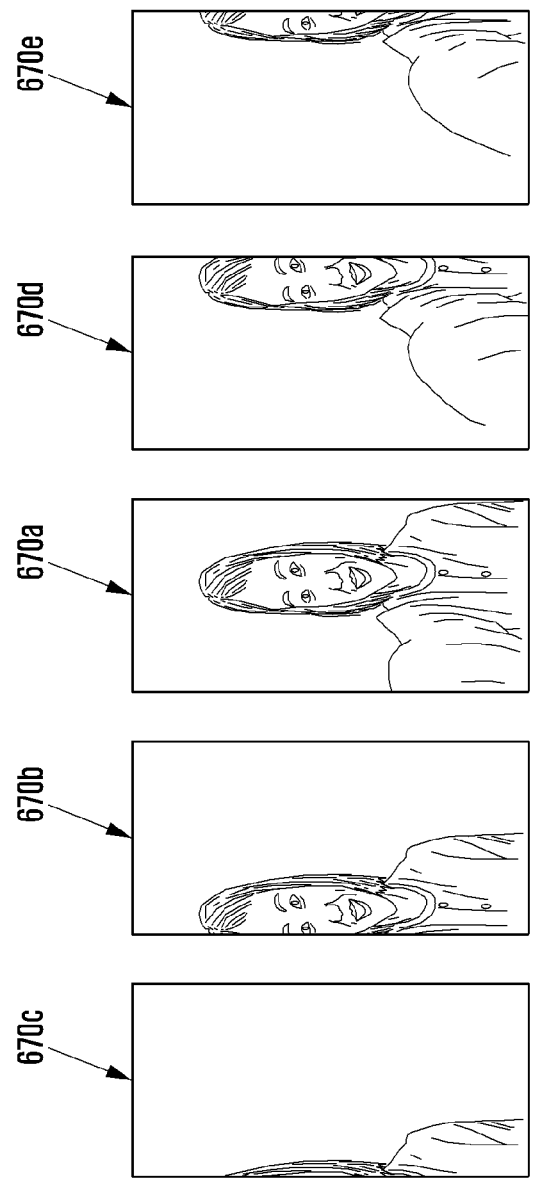
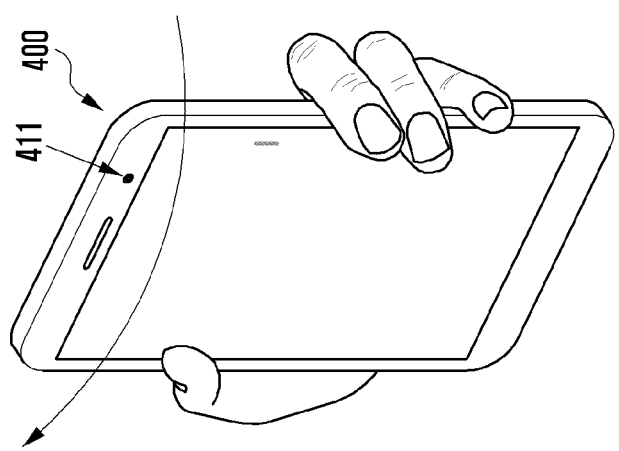

METHOD FOR CONTROL OF CAMERA MODULE BASED ON PHYSIOLOGICAL SIGNAL

PRIORITY

This application claims priority under 35 U.S.C. §119(a) to Korean Patent Application No. 10-2014-0116510 filed in the Korean Intellectual Property Office on Sep. 2, 2014, the entire content of which is incorporated herein by reference.

BACKGROUND

1. Field of the Invention

The present invention relates generally to method for a control of a camera module, and more particularly to a method for a control of a camera module based on a physiological signal.

2. Description of the Related Art

Various electronic devices include a camera module, and conventionally acquire an image by either pressing a photography button mounted to a body of the electronic device or by touching a photography button displayed on a display.

However, an operation of manipulating a mechanical button or a button image on a display may influence the quality of the acquired image.

SUMMARY

The present invention has been made to address at least the problems and disadvantages described above and to provide at least the advantages described below.

Accordingly, an aspect of the present invention is to provide a method of image acquisition through a camera module of an electronic device without manipulating a mechanical button or a virtual button displayed on a display of the electronic device.

Accordingly, another aspect of the present invention is to provide a method of controlling a camera module of an electronic device by using physiological information.

Accordingly, another aspect of the present invention is to allow a user to control a camera module of an electronic device by using a sensor module. For example, a user of an electronic device can change a setting of the camera module or instruct to acquire an image based on a motion of a finger on the sensor module.

Accordingly, another aspect of the present invention is to acquire an image through a camera module of the electronic device which can be processed based on physiological information or emotional information received by the sensor module.

In accordance with an aspect of the present invention, a method of controlling an electronic device is provided. The method includes receiving an input signal including a physiological signal of a subject to be examined through a sensor module of the electronic device, detecting an input operation based on at least the input signal, and acquiring an image through a camera module according to the input operation. In accordance with another aspect of the present invention, an electronic device is provided. The electronic device includes a camera module, a sensor module that receives an input signal including a physiological signal of a subject to be examined, and a control module that detects an input operation at least based on the input signal and acquiring an image through the camera module according to the input operation.

In accordance with another aspect of the present invention, a method is provided. The method includes receiving a physiological signal of a user through a biometric sensor of an electronic device, and acquiring an image through a camera module of the electronic device at least based on a change in the physiological signal. In accordance with another aspect of the present invention, a mobile terminal is provided. The mobile terminal includes a camera module arranged on at least one of a front surface and a rear surface of a body of the mobile terminal, a sensor module for receiving a physiological signal of a user, the sensor module being formed on at least one of the front surface and the rear surface of the body, and a control module for acquiring an image through the camera module at least based on a change in the physiological signal, the control module being functionally connected to the camera module and the sensor module. In accordance with another aspect of the present invention, a non-transitory computer-readable recording medium having a program recorded thereon to perform a method is provided. The method includes receiving a physiological signal of a user through a biometric sensor of an electronic device, and acquiring an image through a camera module of the electronic device at least based on a change in the physiological signal.

BRIEF DESCRIPTION OF THE DRAWINGS

The above and other aspects, features and advantages of the present invention will be more apparent from the following detailed description taken in conjunction with the accompanying drawings, in which:

FIG. 14 illustrates controlling an electronic device based on a contact sequence, according to an embodiment of the present invention;

FIGS. 15A and 15B illustrate controlling an electronic device based on a movement direction, according to an embodiment of the present invention;

FIGS. 27A to 27D illustrate a method of controlling an electronic device to photograph a panorama image, according to an embodiment of the present invention.

DETAILED DESCRIPTION OF EMBODIMENTS OF THE PRESENT INVENTION

Figure 1:
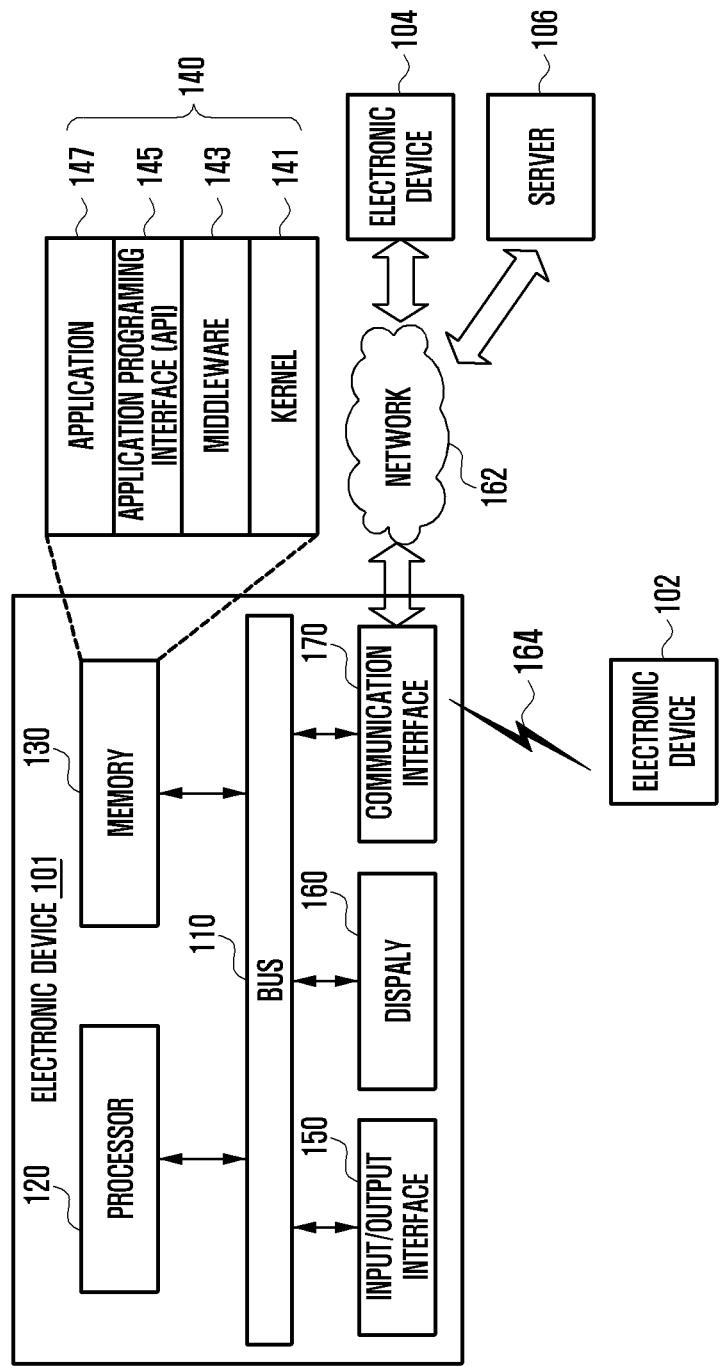
FIG. 1 is a block diagram of an electronic device within a network environment, according to an embodiment of the present invention.

The following description with reference to the accompanying drawings is provided to assist in a comprehensive understanding of various embodiments of the present invention as defined by the claims and their equivalents. It includes various specific details to assist in that understanding, but these are to be regarded as merely as examples. Accordingly, those of ordinary skill in the art will recognize that various changes and modifications of the various embodiments described herein can be made without departing from the scope and spirit of the present invention. In addition, descriptions of well-known functions and constructions may be omitted for clarity and conciseness.

The terms and words used in the following description and claims are not limited to their dictionary meanings, but, are merely used to enable a clear and consistent understanding of the present invention. Accordingly, it should be apparent to those skilled in the art that the following description of various embodiments of the present invention is provided for illustration purposes only and not for the purpose of limiting the present invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

An electronic device according to an embodiment of the present invention may be an apparatus having a communication function. For example, the electronic device according to the present invention may be at least one of and/or combinations of a smart phone, a tablet Personal Computer (PC), a mobile phone, a video phone, an electronic-boot (e-book) reader, a desktop PC, a laptop PC, a netbook computer, a Personal Digital Assistant (PDA), a Portable Multimedia Player (PMP), an MP3 player, a mobile medical appliance, an electronic bracelet, an electronic necklace, an electronic accessory, a camera, a wearable device, an electronic clock, a wrist watch, home appliances (e.g., a refrigerator, an air conditioner, a cleaner, an oven, a microwave oven, a washing machine, an air cleaner, etc.), an artificial intelligence robot, a television (TV), a Digital Versatile Disk (DVD) player, an audio player, various medical appliances (e.g., a Magnetic Resonance Angiography (MRA) device, a Magnetic Resonance Imaging (MRI) device, a Computerized Tomography (CT) device, an ultrasonography device etc.), a navigation device, a Global Positioning System (GPS) receiver, an Event Data Recorder (EDR), a Flight Data Recorder (FDR), a set-top box, a TV box (e.g., HomeSync™ of SAMSUNG Electronics, Co., Apple TV™ of APPLE, Co., and Google TV™ of Google, Co.), an electronic dictionary, an infotainment device for a vehicle, an electronic equipment for a ship (e.g., a navigation device, a gyrocompass, etc.), an avionic device, a security device, an electronic cloth, an electronic key, a camcorder, a game console, a Head-Mounted Display (HMD) unit, a flat panel display device, an electronic frame, an electronic album, a piece of furniture having a communication function and/or a part of a building/structure, an electronic board, an electronic signature receiving device, and a protector.

It should be obvious to those skilled in the art that the electronic device according to the present invention is not limited to the aforementioned devices.

FIG. 1 is a block diagram of an electronic device within a network environment, according to an embodiment of the present invention.

Referring to FIG. 1, the electronic device 101 includes a bus 110, a processor 120, a memory 130, a input/output interface 150, a display 160, and a communication interface 170.

The bus 110 is a circuit for interconnecting the elements described above, e.g., the processor 120, the memory 130, the input/output interface 150, the display 160, and the communication interface 170, and for allowing a communication, e.g., by transferring a control message, between the elements described above.

The processor 120 receives commands from the abovementioned other elements, e.g. the memory 130, the input/output interface 150, the display 160, and the communication interface 170, through, for example, the bus 110, deciphers the received commands, and performs operations and/or data processing according to the deciphered commands.

The memory 130 stores commands received from the processor 120 and/or other elements, e.g. the input/output interface 150, the display 160, and the communication interface 170, and/or commands and/or data generated by the processor 120 and/or other elements. The memory 130 include software and/or programs 140, such as a kernel 141, middleware 143, an Application Programming Interface (API) 145, and an application 147. Each of the programming modules described above may be configured by software, firmware, hardware, and/or combinations of two or more thereof.

The kernel 141 controls and/or manages system resources, e.g. the bus 110, the processor 120 or the memory 130, used for execution of operations and/or functions implemented in other programming modules, such as the middleware 143, the API 145, and/or the application 147. Further, the kernel 141 provides an interface through which the middleware 143, the API 145, and/or the application 147 can access and then control and/or manage an individual element of the electronic device 101.

The middleware 143 performs a relay function which allows the API 145 and/or the application 147 to communicate with and exchange data with the kernel 141. Further, in relation to operation requests received from at least one of an application 147, the middleware 143 performs load balancing in relation to the operation requests by, for example, giving a priority in using a system resource, e.g., the bus 110, the processor 120, and/or the memory 130, of the electronic device 101 to at least one application from among the at least one of the application 147.

The API 145 is an interface through which the application 147 controls a function provided by the kernel 141 and/or the middleware 143, and includes, for example, at least one interface or function for file control, window control, image processing, and/or character control.

The input/output interface 150 receives a command and/or data from a user, and transfers the received command and/or data to the processor 120 and/or the memory 130 through the bus 110. The display 160 displays an image, a video, and/or data to a user.

The communication interface 170 establishes a communication between the electronic device 101 and a first external device 102, a second external device 104, and/or a server 106. The communication interface 170 supports short range communication protocols, e.g., a WiFi protocol, a BlueTooth (BT) protocol, and a Near Field Communication (NFC) protocol, communication networks (e.g., Internet, Internet of Things (IoT), Local Area Network (LAN), Wire Area Network (WAN), a telecommunication network, a cellular network, and a satellite network), a Plain Old Telephone Service (POTS), or any other similar and/or suitable communication networks, such as network 162. Each of the first and second external devices 102 and 104 may be a same type and/or different types of electronic devices.

Figure 2:
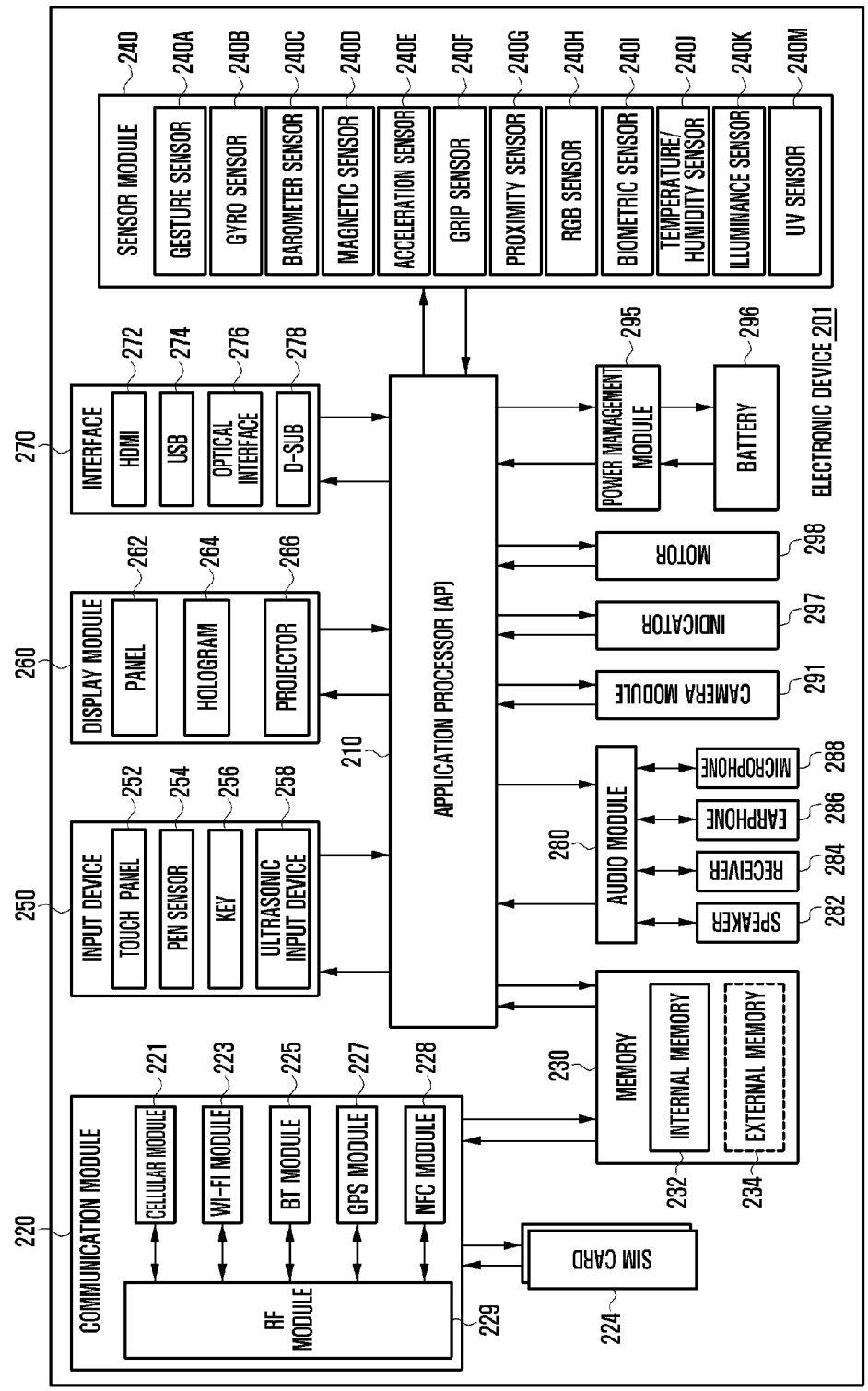
FIG. 2 is a block diagram of a configuration of an electronic device, according to an embodiment of the present invention.

FIG. 2 is a block diagram of a configuration of an electronic device, according to an embodiment of the present invention.

Referring to FIG. 2, a block diagram of an electronic device 201 is provided. The electronic device 201 may configure a whole or a part of the electronic device 101 illustrated in FIG. 1. The electronic device 201 includes one or more Application Processors (APs) 210, a communication module 220, a Subscriber Identification Module (SIM) card 224, a memory 230, a sensor module 240, an input device 250, a display module 260, an interface 270, an audio module 280, a camera module 291, a power management module 295, a battery 296, an indicator 297, and a motor 298.

The AP 210 operates an Operating System (OS) or an application program so as to control a plurality of hardware or software component elements connected to the AP 210 and execute various data processing and calculations including multimedia data. The AP 210 may be implemented by, for example, a System on Chip (SoC). The processor 210 may further include a Graphic Processing Unit (GPU).

The communication module 220 transmits/receives data in communication between different electronic devices, e.g., the second external device 104 and the server 106, connected to the electronic device 201 through the network 162. According to an embodiment, the communication module 220 includes a cellular module 221, a WiFi module 223, a BlueTooth (BT) module 225, a Global Positioning System (GPS) module 227, a Near Field Communication (NFC) module 228, and a Radio Frequency (RF) module 229.

The cellular module 221 provides a voice, a call, a video call, a Short Message Service (SMS), or an Internet service through a communication network (for example, Long Term Evolution (LTE), LTE-Advanced (LTE-A), Code Division Multiple Access (CDMA), Wideband CDMA (WCDMA), Universal Mobile Telecommunication System (UMTS), Wireless Broadband (WiBro), Global System for Mobile communication (GSM), etc.). Further, the cellular module 221 authenticates electronic devices within a communication network by using a the SIM card 224. According to an embodiment, the cellular module 221 performs at least some of the functions which can be provided by the AP 210. For example, the cellular module 221 may perform at least some of the multimedia control functions.

The cellular module 221 may include a Communication Processor (CP). Further, the cellular module 221 may be implemented by, for example, an SoC.

Although the components such as the cellular module 221 (for example, communication processor), the memory 230, and the power management module 295 are illustrated as components separate from the AP 210 in FIG. 2, the AP 210 may include at least some (for example, cellular module 221) of the aforementioned components in an embodiment.

The AP 210 or the cellular module 221 (for example, communication processor) loads a command or data received from at least one of a non-volatile memory and other components connected to each of the AP 210 and the cellular module 221 to a volatile memory and processes the loaded command or data. Further, the AP 210 or the cellular module 221 stores data received from at least one of other components or generated by at least one of other components in a non-volatile memory.

Each of the WiFi module 223, the BT module 225, the GPS module 227, and the NFC module 228 may include, for example, a processor for processing data transmitted/received through the corresponding module. Although the cellular module 221, the WiFi module 223, the BT module 225, the GPS module 227, and the NFC module 228 are illustrated as blocks separate from each other in FIG. 2, at least some of the cellular module 221, the WiFi module 223, the BT module 225, the GPS module 227, and the NFC module 228 may be included in one Integrated Chip (IC) or one IC package according to one embodiment. For example, at least some (for example, the communication processor corresponding to the cellular module 221 and the WiFi processor corresponding to the WiFi module 223) of the processors corresponding to the cellular module 221, the WiFi module 223, the BT module 225, the GPS module 227, and the NFC module 228 may be implemented by one SoC.

The RF module 229 transmits/receives data, for example, an RF signal. The RF module 229 may include, for example, a transceiver, a Power Amp Module (PAM), a frequency filter, a Low Noise Amplifier (LNA), etc. Further, the RF module 229 may include a component for transmitting/receiving electronic waves over a free air space in wireless communication, for example, a conductor, a conducting wire, etc. Although the cellular module 221, the WiFi module 223, the BT module 225, the GPS module 227, and the NFC module 228 share one RF module 229 in FIG. 2, at least one of the cellular module 221, the WiFi module 223, the BT module 225, the GPS module 227, and the NFC module 228 may transmit/receive an RF signal through a separate RF module.

The SIM card 224 is a card that may be inserted into a slot formed in a particular portion of the electronic device 201. The SIM card 224 includes unique identification information (for example, Integrated Circuit Card IDentifier (ICCID)) or subscriber information (for example, International Mobile Subscriber Identity (IMSI)).

The memory 230 includes an internal memory 232 or an external memory 234.

The internal memory 232 may include at least one of a volatile memory (for example, a Random Access Memory (RAM), a Dynamic RAM (DRAM), a Static RAM (SRAM), a Synchronous Dynamic RAM (SDRAM), etc.), and a non-volatile memory (for example, a Read Only Memory (ROM), a One Time Programmable ROM (OTPROM), a Programmable ROM (PROM), an Erasable and Programmable ROM (EPROM), an Electrically Erasable and Programmable ROM (EEPROM), a mask ROM, a flash ROM, a NAND flash memory, an NOR flash memory, etc.).

The internal memory 232 may be a Solid State Drive (SSD).

The external memory 234 may include a flash drive, for example, a Compact Flash (CF), a Secure Digital (SD), a Micro Secure Digital (Micro-SD), a Mini Secure Digital (Mini-SD), an extreme Digital (xD), or a memory stick. The external memory 234 may be functionally connected to the electronic device 201 through various interfaces. The electronic device 201 may further include a storage device (or storage medium) such as a hard drive.

The sensor module 240 measures a physical quantity or detects an operation state of the electronic device 201, and converts the measured or detected information to an electronic signal. The sensor module 240 may include at least one of a gesture sensor 240A, a gyro sensor 240B, an atmospheric pressure (barometric) sensor 240C, a magnetic sensor 240D, an acceleration sensor 240E, a grip sensor 240F, a proximity sensor 240G, a color sensor 240H (for example, Red, Green, and Blue (RGB) sensor) 240H, a biometric sensor 240I, a temperature/humidity sensor 240J, an illuminance (light) sensor 240K, and a Ultra Violet (UV) sensor 240M. Additionally or alternatively, the sensor module 240 may include, for example, a E-nose sensor, an electromyography (EMG) sensor, an electroencephalogram (EEG) sensor, an electrocardiogram (ECG) sensor, an Infra-Red (IR) sensor, an iris sensor, a fingerprint sensor, etc. The sensor module 240 may further include a control circuit for controlling one or more sensors included in the sensor module 240.

The input device 250 includes a touch panel 252, a (digital) pen sensor 254, a key 256, and an ultrasonic input device 258. For example, the touch panel 252 recognize a touch input in at least one type of a capacitive type, a resistive type, an infrared type, and an acoustic wave type. The touch panel 252 further include a control circuit. In the capacitive type, the touch panel 252 can recognize proximity as well as a direct touch. The touch panel 252 further include a tactile layer. In this event, the touch panel 252 provides a tactile reaction to the user.

The (digital) pen sensor 254 may be implemented, for example, using a method identical or similar to a method of receiving a touch input of the user, or using a separate recognition sheet.

The key 256 may include a physical button, an optical key, or a key pad.

The ultrasonic input device 258 is a device which detects an acoustic wave by microphone 288 of the electronic device 201 through an input means generating an ultrasonic signal to identify data and performs wireless recognition.

The electronic device 201 may receive a user input from the first or second external device 102 and 104 or the server 106 connected to the electronic device 201 by using the communication module 220.

The display module 260 includes a panel 262, a hologram device 264, and a projector 266.

The panel 262 may be, for example, a Liquid Crystal Display (LCD) or an Active Matrix Organic Light Emitting Diode (AM-OLED). The panel 262 may be implemented to be, for example, flexible, transparent, or wearable. The panel 262 may be configured by the touch panel 252 and one module.

The hologram device 264 displays a stereoscopic image in the air by using interference of light.

The projector 266 projects light on a screen to display an image. The screen may be located inside or outside the electronic device 201.

The display module 260 may further include a control circuit for controlling the panel 262, the hologram device 264, and the projector 266.

The interface 270 includes a High-Definition Multimedia Interface (HDMI) 272, a Universal Serial Bus (USB) 274, an optical interface 276, and a D-subminiature (D-sub) 278. The interface 270 may be included in the communication interface 160 illustrated in FIG. 1. Additionally or alternatively, the interface 290 may include, for example, a Mobile High-definition Link (MHL) interface, a Secure Digital (SD) card/Multi-Media Card (MMC), or an Infrared Data Association (IrDA) standard interface.

The audio module 280 bi-directionally converts a sound and an electronic signal. At least some components of the audio module 280 may be included in the input/output interface 140 illustrated in FIG. 1. The audio module 280 processes sound information input or output through a speaker 282, a receiver 284, an earphone 286, and the microphone 288.

The camera module 291 is a device which can photograph a still image and a video. The camera module 291 may include one or more image sensors (for example, a front sensor or a back sensor), an Image Signal Processor (ISP) or a flash (for example, an LED or xenon lamp).

The power management module 295 manages power of the electronic device 201. The power management module 295 may include, for example, a Power Management Integrated Circuit (PMIC), a charger Integrated Circuit (IC), or a battery gauge.

The PMIC may be mounted to an integrated circuit or an SoC semiconductor. A charging method is divided into wired and wireless methods. The charger IC charges a battery and prevents over voltage or over current from flowing from a charger. The charger IC includes a charger IC for at least one of the wired charging method and the wireless charging method.

The wireless charging method may include a magnetic resonance method, a magnetic induction method and an electromagnetic wave method, and additional circuits for wireless charging, for example, circuits such as a coil loop, a resonant circuit, a rectifier, etc. may be added.

The battery gauge measures, for example, a remaining quantity of the battery 296, or a voltage, a current, or a temperature during charging.

The battery 296 stores or generates electricity and supplies power to the electronic device 201 by using the stored or generated electricity. The battery 296 may include a rechargeable battery or a solar battery.

The indicator 297 shows particular statuses of the electronic device 201 or a part (for example, AP 210) of the electronic device 201, for example, a booting status, a message status, a charging status, etc.

The motor 298 converts an electrical signal to a mechanical vibration.

The electronic device 201 may include a processing unit (for example, GPU) for supporting a module TV. The processing unit for supporting the mobile TV may process media data according to a standard of Digital Multimedia Broadcasting (DMB), Digital Video Broadcasting (DVB), media flow, etc.

Each of the components of the electronic device according to various embodiments of the present invention may be implemented by one or more components and the name of the corresponding component may vary depending on a type of the electronic device. The electronic device according to various embodiments of the present invention may include at least one of the above described components, a few of the components may be omitted, or additional components may be further included. Also, some of the components of the electronic device according to various embodiments of the present invention may be combined to form a single entity, and thus may equivalently execute functions of the corresponding components before being combined.

Figure 3:
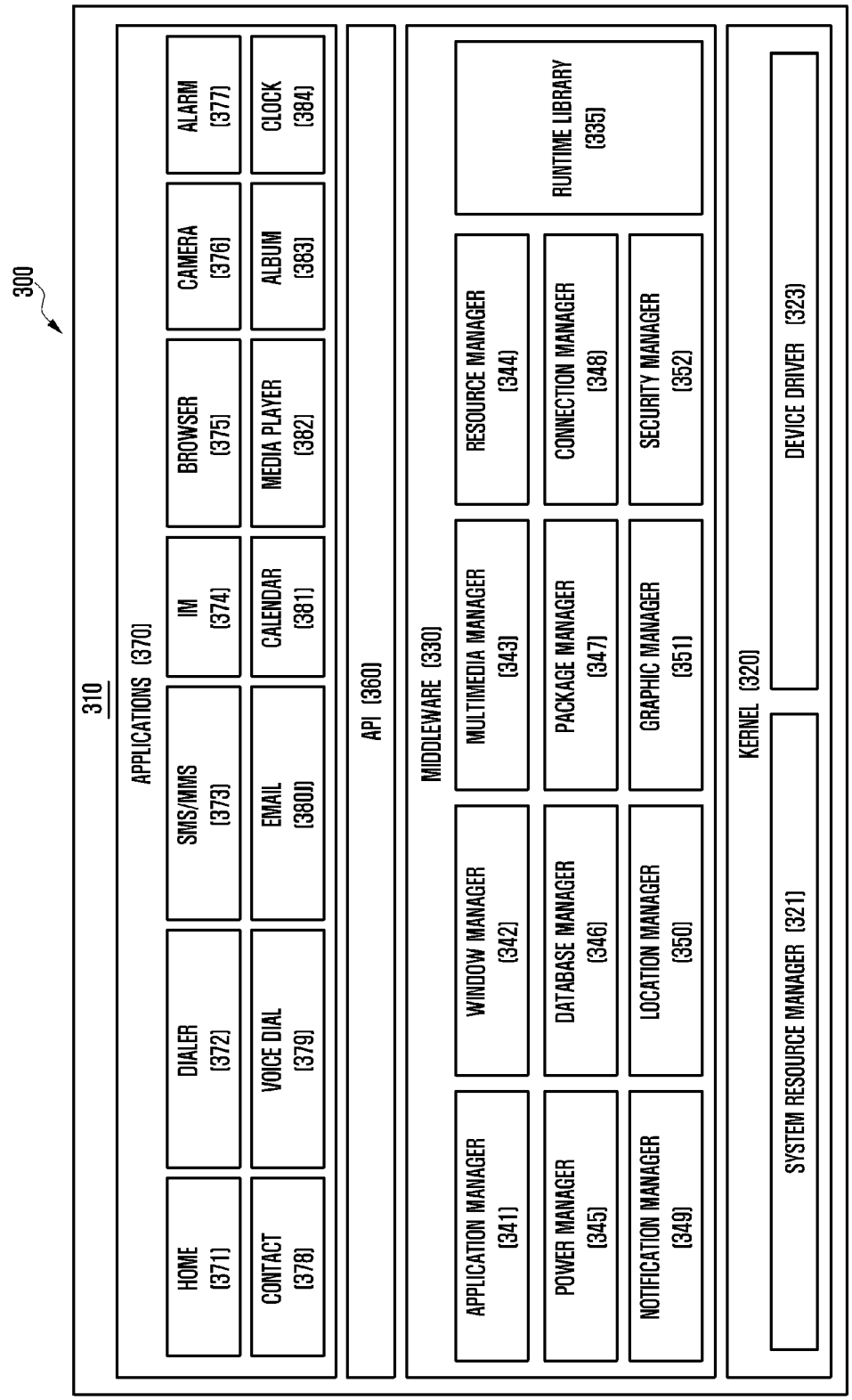
FIG. 3 is a block diagram of a programming module of an electronic device, according to an embodiment of the present invention.

FIG. 3 is a block diagram of a programming module of an electronic device, according to an embodiment of the present invention;

Referring to FIG. 3 a block diagram of a programming module 300 is provided. The programming module 300 may be included (stored) in the electronic device 101 (for example, memory 130) illustrated in FIG. 1. At least some of the programming module 300 may be formed of software, firmware, hardware, or a combination of software, firmware, and hardware. The programming module 300 may be executed in the hardware (for example, electronic device 201) to include an Operating System (OS) controlling resources related to the electronic device 101 or various applications 370 driving on the OS. For example, the OS is Android™, iOS™, Windows™, Symbian™, Tizen™, Bada™, etc. The programming module 300 includes a kernel 320, a middleware 330, an Application Programming Interface (API) 360, and the applications 370.

The kernel 320 includes a system resource manager 321 and a device driver 323.

The system resource manager 321 may include, for example, a process manager, a memory manager, and a file system manager. The system resource manager 311 performs a system resource control, allocation, and recall.

The device driver 323 may include, for example, a display driver, a camera driver, a Bluetooth driver, a shared memory driver, a USB driver, a keypad driver, a WiFi driver, and an audio driver. Further, according to an embodiment, the device driver 312 include an Inter-Process Communication (IPC) driver.

The middleware 330 includes a plurality of modules prepared in advance to provide a function required in common by the applications 370. Further, the middleware 330 provides a function through the API 360 to allow the applications 370 to efficiently use limited system resources within the electronic device 101. The middleware 300 includes at least one of a runtime library 335, an application manager 341, a window manager 342, a multimedia manager 343, a resource manager 344, a power manager 345, a database manager 346, a package manager 347, a connection manager 348, a notification manager 349, a location manager 350, a graphic manager 351, and a security manager 352.

The runtime library 335 includes a library module used by a complier to add a new function through a programming language while the application 370 is executed. The runtime library 335 executes input and output, management of a memory, a function associated with an arithmetic function, etc.

The application manager 341 manages a life cycle of at least one of the applications 370.

The window manager 342 manages GUI resources used on the screen.

The multimedia manager 343 detects a format required for reproducing various media files and performs an encoding or a decoding of a media file by using a codec suitable for the corresponding format.

The resource manager 344 manages resources such as a source code, a memory, or a storage space of at least one of the applications 370.

The power manager 345 operates together with a Basic Input/Output System (BIOS) to manage a battery or power and provides power information required for the operation.

The database manager 346 manages generation, search, and change of a database to be used by at least one of the applications 370.

The package manager 347 manages an installation or an update of an application distributed in a form of a package file.

The connection manager 348 manages a wireless connection, such as WiFi or Bluetooth.

The notification manager 349 displays or notifies a user of an event, such as an arrival message, an appointment, a proximity alarm, etc., in a manner that does not disturb the user.

The location manager 350 manages location information of the electronic device 101.

The graphic manager 351 manages a graphic effect provided to the user or a user interface related to the graphic effect.

The security manager 352 provides a general security function required for a system security or a user authentication.

When the electronic device 101 has a call function, the middleware 330 may further include a telephony manager for managing a voice or a video call function of the electronic device 101.

The middleware 330 may generate a new middleware module through a combination of various functions of the aforementioned internal component modules and use the generated new middleware module. The middleware 330 may provide a module specific to each type of operating system to provide a differentiated function. Further, the middleware 330 may dynamically delete some of the conventional components or add new components. Accordingly, some of the components described in the embodiment of the present invention may be omitted, replaced with other components having different names but performing similar functions, or other components may be further included.

The API 360 is a set of API programming functions, and may be provided with a different configuration according to an operating system. For example, in Android™ or iOS™, a single API set may be provided for each platform. In Tizen™, two or more API sets may be provided.

The applications 370 may include a preloaded application and/or a third party application. The applications 370 may include a home application 371, a dialer application 372, a Short Messaging Service (SMS)/Multimedia Messaging Service (MMS) application 373, an Instant Messaging (IM) application 374, a browser application 375, a camera application 376, an alarm application 377, a contact application 378, a voice dial application 379, an email application 380, a calendar application 381, a media player application 382, an album application 383, and a clock application 384. However, the present embodiment is not limited thereto, and the applications 370 may include any other similar and/or suitable application.

At least some of the programming module 300 is implemented by a command stored in a computer-readable storage medium. When the command is executed by one or more processors (for example, processor 210), the one or more processors perform a function corresponding to the command. The computer-readable storage medium may be, for example, the memory 260. At least some of the programming module 300 may be implemented (for example, executed) by, for example, the processor 210. At least some of the programming module 300 may include, for example, a module, a program, a routine, sets of instructions, or a process for performing one or more functions.

According to an embodiment of the present invention, the names of the components of the programming module 300 may vary depending on a type of operating system. Further, the programming module 300 may include one or more of the aforementioned components, omit some of the components, or further include other additional components.

Figure 4:
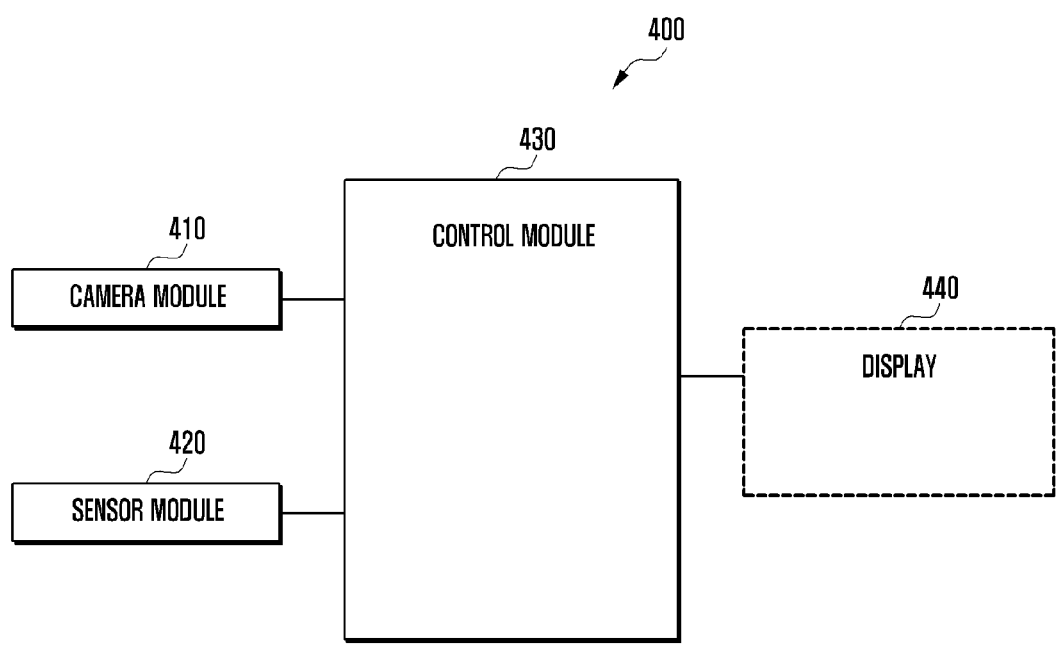
FIG. 4 is a block diagram of an electronic device, according to an embodiment of the present invention.

FIG. 4 is a block diagram of an electronic device, according to an embodiment of the present invention.

Referring to FIG. 4, an electronic device 400 is provided. The electronic device 400 includes a camera module 410, a sensor module 420, and a control module 430. The electronic device may additionally include a display 440. The electronic device 400 may be the electronic device 101 described with reference to FIG. 1 or the electronic device 201 described with reference to FIG. 2.

The camera module 410 may include one or more image sensors for photographing a still image or a moving image. The camera module 410 changes the settings of the one or more image sensors according to a control command or a signal. For example, the camera module 410 controls the focus, white balance, a shutter speed, or brightness according to the control command. Further, the camera module 410 controls the one or more image sensors to acquire images according to the control command or the signal.

The sensor module 420 measures or detects a physical quantity related to the electronic device 400 or a physiological signal of a subject to be examined and converts the detected physical quantity or physiological signal into an electrical signal. The sensor module 420 includes a biometric sensor for measuring the physiological signal of the subject to be examined.

The biometric sensor may be a Photoplethysmography (PPG) sensor for the subject to be examined. The biometric sensor measures a physiological signal, including at least one of iris information, retina information, vein information, fingerprint information, and Saturation of peripheral Oxygen (SpO2).

The biometric sensor may, alternatively, be a Heart Rate Monitor (HRM), a Heart Rate Variability (HRV) sensor, an electromyogram sensor, or an electroencephalogram sensor.

Alternatively, the sensor module 420 may include at least one of an illumination sensor, a gesture sensor, an acceleration sensor, a location sensor, a gyroscope sensor, and a magnetic sensor, as well as the biometric sensor.

The sensor module 420 is configured to receive an input signal, and the input signal includes a physiological signal of the subject to be examined and information on a physical quantity related to the electronic device 400. The subject to be examined may be a user of the electronic device 400.

The control module 430 is functionally connected to the camera module 410 and the sensor module 420, and controls the camera module 410 to acquire an image at least based on the input signal received through the sensor module 420. The physiological signal is included in the input signal for controlling the camera module 410. A control command or a signal for the camera module 410 is an input operation detected based on the input signal received through the sensor module 420. The input operation includes an operation by the subject to be examined with respect to at least a part of the surface of the sensor module 420, for example, an approach operation, a contact operation, or a separation operation.

The display 440 displays a dynamic image acquired through the camera module 410, for example, a preview image. The display 440 displays a still image acquired through the camera module 410, for example, a photographed image. Further, the display 440 may display various User Interfaces (UIs) for controlling the camera module 410 by the control module 430.

The electronic device 400 may further include the audio module 280. In this case, the control module 430 is functionally connected to the audio module 280 and the sensor module 420, and controls the audio module 280 to acquire audio data at least based on the input signal received through the sensor module 420. The physiological signal is included in the input signal for controlling the audio module. A control command or a signal for the audio module is an input operation detected based on the input signal received through the sensor module 420. The input operation includes an operation by the subject to be examined with respect to at least a part of the surface of the sensor module 420, for example, an approach operation, a contact operation, or a separation operation.

The electronic device 400 may additionally include the communication module 220. In this case, the control module 430 is connected to the communication module and the sensor module 420 and also functionally connected to at least one of the display 440 and the audio module, and controls at least one of the display 440 and the audio module 220 to acquire an image or audio data at least based on the input signal received through the sensor module 420. The physiological signal is included in the input signal for controlling the display 440 or the audio module. A control command or a signal for the display 440 or the audio module is an input operation detected based on the input signal received through the sensor module 420. The input operation includes an operation by the subject to be examined with respect to at least a part of the surface of the sensor module 420, for example, an approach operation, a contact operation, or a separation operation. For example, the control module 430 acquires an image (for example, a call application screen or a conference application screen) or a video (for example, a video including one or more of a recipient image and a sender image) displayed on the display 440 at least based on the input signal received through the sensor module 420 during a voice call, a video call, an audio conference, or a video conference. Alternatively, the control module 430 acquires one or more of the audio signals output or input through the audio module 280.

Figure 5A:
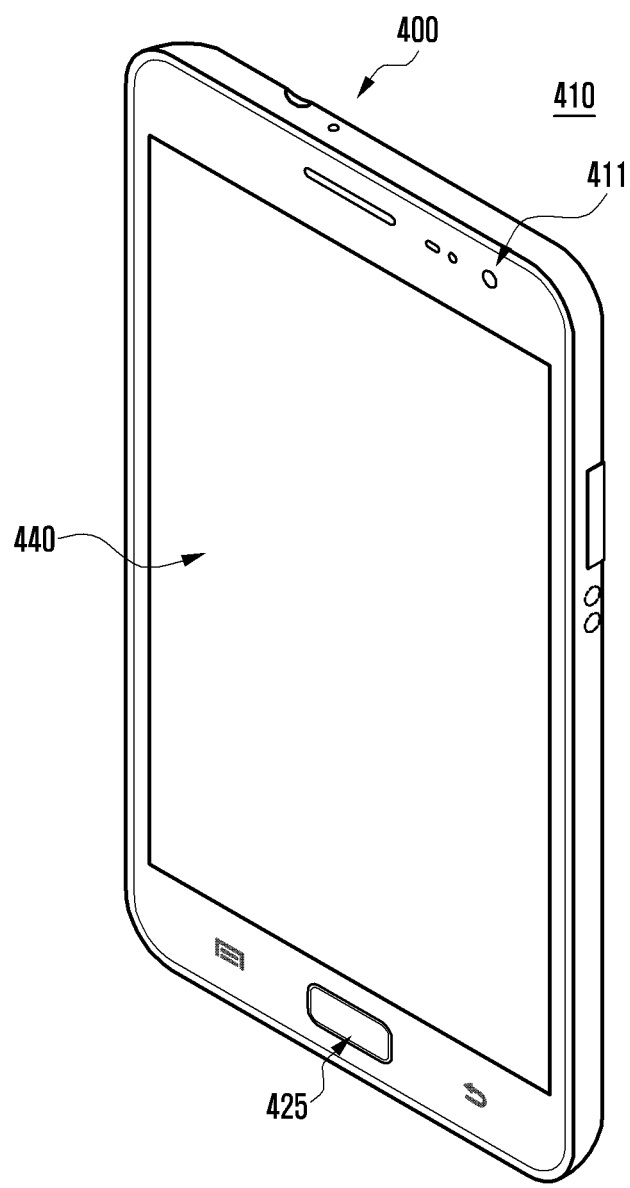
FIGS. 5A and 5B are perspective views of an electronic device, according to an embodiment of the present invention.
Figure 5B:
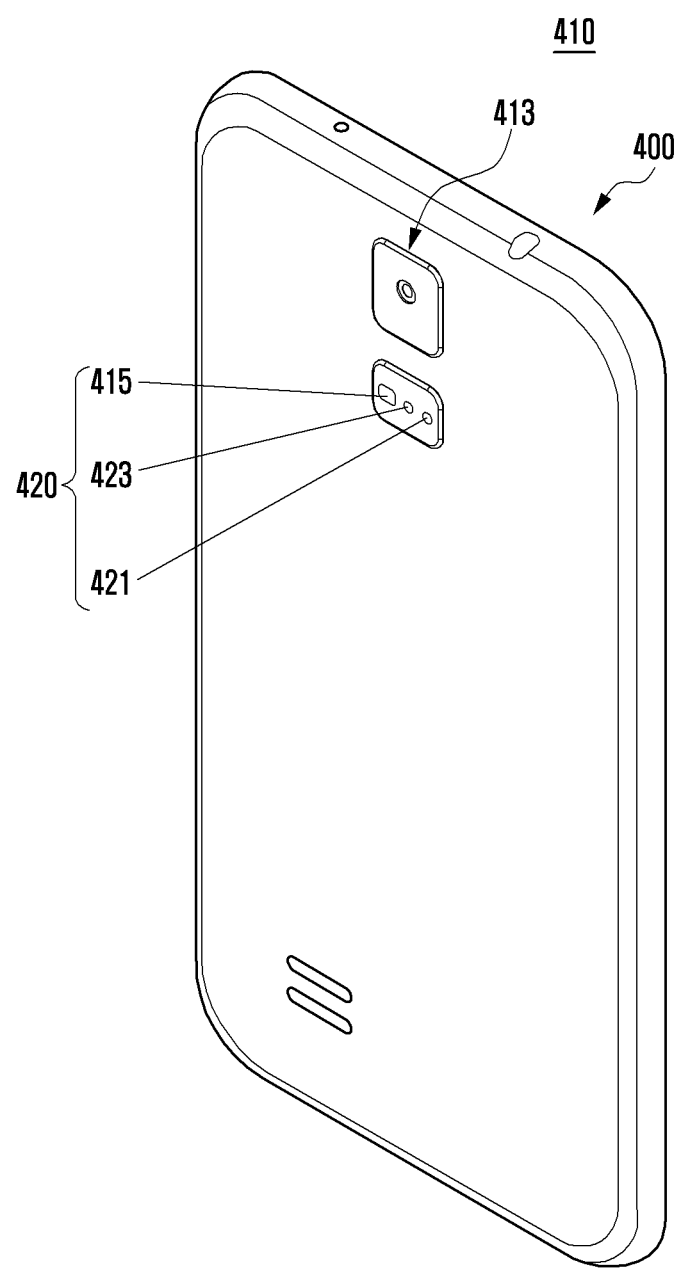

FIGS. 5A and 5B are perspective views of an electronic device, according to an embodiment of the present invention.

Referring to FIG. 5A, a front perspective view of an electronic device 400 is provided. Electronic device 400 includes a bar type terminal body, however, the electronic device of the present invention is not limited to thereto and may have various structures such as a scroll type, a curvedly bent type, a slide type in which two or more bodies are coupled to reciprocally move, and a folder type.

As illustrated in FIG. 5A, the electronic device 400 includes a front surface, a side surface, and a rear surface, and includes both ends formed along a length direction. The body includes a case forming the exterior of the electronic device 400, and the case may be classified into a front case and a rear case. Various types of components included in the electronic device 400 may be arranged in the space formed between the front case and the rear case. When the electronic device 400 corresponds to the electronic device 201 disclosed with reference to FIG. 2, the components included in the electronic device 201 may be located in the case or may be located in the space formed between the front case and the rear case. For example, the camera module 410, the sensor module 420, a button 425, and the display 440 may be located in the case included in the body of the electronic device 400. The display 440 occupies a main part of the front case. The camera module 410 may be located in at least one of the front case and the rear case included in the body of the electronic device 400. As shown in FIG. 5A, the camera module 411 is arranged on the front case of the electronic device 400 and is located in an area close to one of the end parts of the display 440.

Referring to FIG. 5B, a rear perspective view of an electronic device 400 is provided. As shown in FIG. 5B, the camera module 413 is arranged on the rear surface of the body of the electronic device 400 and is located in the rear case.

The front camera module 411 and the rear camera module 413 may have different photographing directions. The rear camera module 413 may be configured to be capable of performing photography in higher definition than the front camera module 411. A flash 415 is disposed in an area adjacent to the rear camera module 413. When the image is acquired through the rear camera module 413, the flash 415 may shine a light toward a subject for photography.

The sensor module 420 is disposed on one surface of the body of the electronic device 400. As shown in FIG. 5B, the sensor module 420 is arranged on the rear surface of the body of the electronic device 400 and is located in the rear case. When the flash 415 is disposed on the rear case, the sensor module 420 is located in an area adjacent to the flash 415. Alternatively, the sensor module 420 may be located in an area adjacent to the rear camera module 413.

Additionally, when the user grasps the electronic device 400 by the hand to acquire an image through the front camera module 411, the sensor module 420 may be disposed on a position of the rear case which user's fingers can reach. In this case, at least some of the user's fingers, which grasp the electronic device 400, may be objects from which the physiological signal is measured by the sensor module 420.

When the button 425 is disposed on the front case, the sensor module 420 may be located in an area adjacent to the button 425 or combined with the button 425.

The biometric sensor included in the sensor module 420 may be an HRM sensor, an HRV sensor, an ECG sensor, or an SpO2 sensor.

The biometric sensor included in the sensor module 420 includes a light emitting unit 421 for generating an incident light and irradiating the light to the subject to be examined and a light receiving unit 423 for receiving a reflected light from the subject to be examined.

The sensor module 420 may be a PPG sensor including the light emitting unit 421 and the light receiving unit 423. The light emitting unit 421 may be implemented as a Light Emitting Diode (LED). Further, the light emitting unit 421 may be implemented as one or more LEDs having different wavelengths. The different wavelengths may be rays including visible rays or infrared rays. The physiological signal, for example, a PPG signal is detected based on the reflected light received through the light receiving unit 423.

Figure 6A:
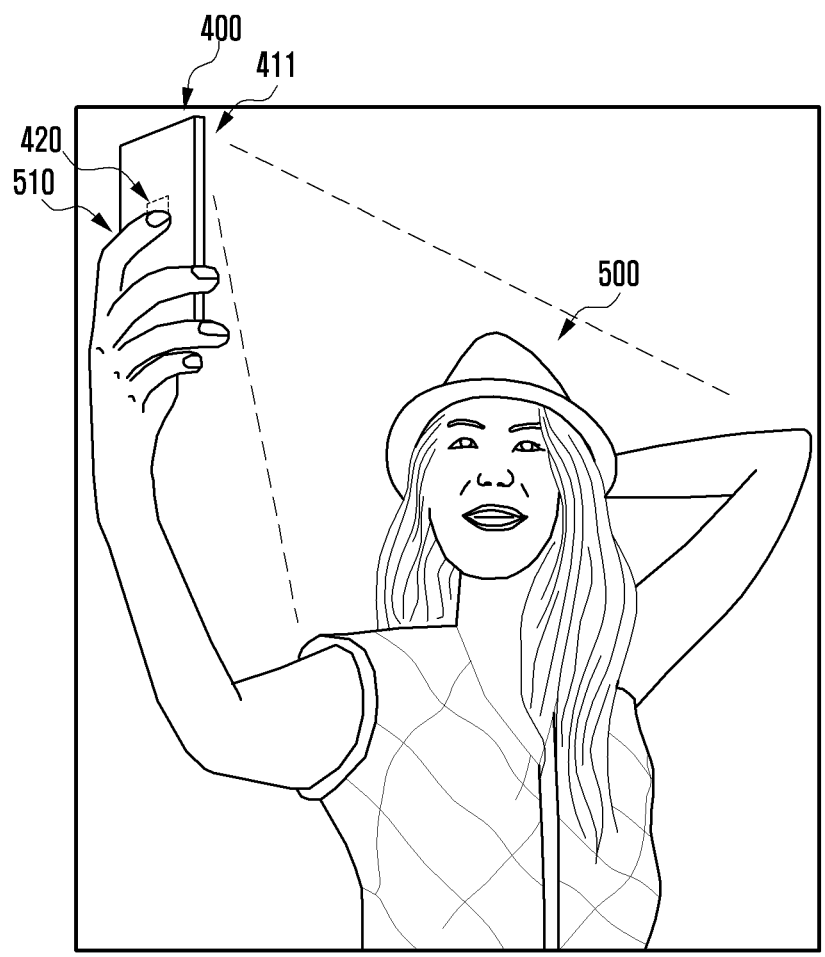
FIGS. 6A to 6C illustrate an operational state of an electronic device, according to an embodiment of the present invention.
Figure 6B:
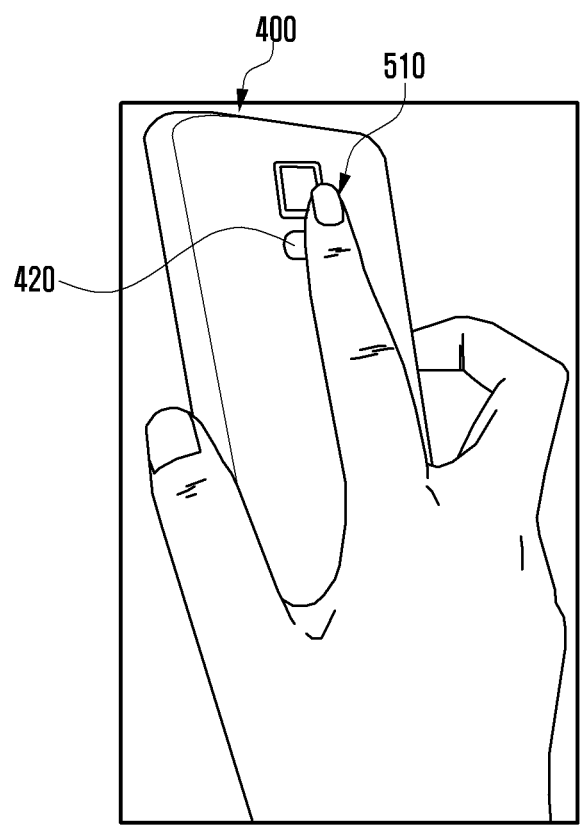
Figure 6C:
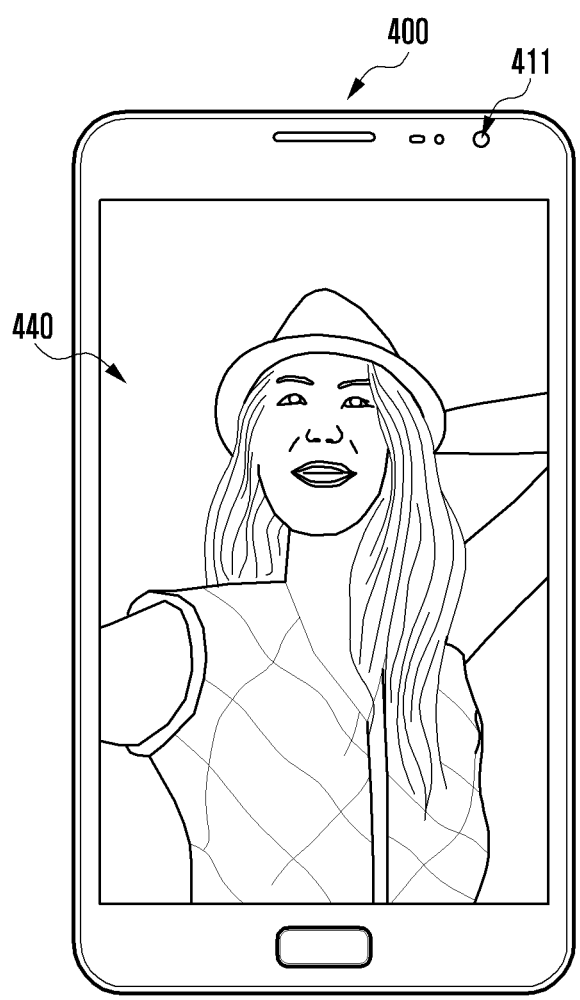

FIGS. 6A to 6C illustrate an operational state of an electronic device, according to an embodiment of the present invention.

Referring to FIG. 6A, a user 500 may place the front camera module 411 located on the front surface of the body of the electronic device 400 toward the user 500 and may control an operation of the front camera module 411 by a subject 510 (such as the user's hand) grasping the body of the electronic device 400.

Referring to FIG. 6B, physiological information on the user 500 is received through the sensor module 420 located in the rear case of the body of the electronic device 400. For example, the electronic device 400 receives, through the sensor module 420 configured to include the biometric sensor, an input signal including physiological information on the subject to be examined, which corresponds to at least a part of the subject 510 (for example, fingers) grasping the body of the electronic device 400. The control module 430 detects an input operation corresponding to a movement of the part of the subject 510, which is the subject to be examined, based on the input signal. The control module 430 then controls the front camera module 411 to acquire an image at least based on the input operation.

Referring to FIG. 6C, the electronic device 400 acquires the image through the camera module 411 based on the input operation on the surface of the sensor module 420 by the subject to be examined and displays the image on the display 440.

Figure 7A:
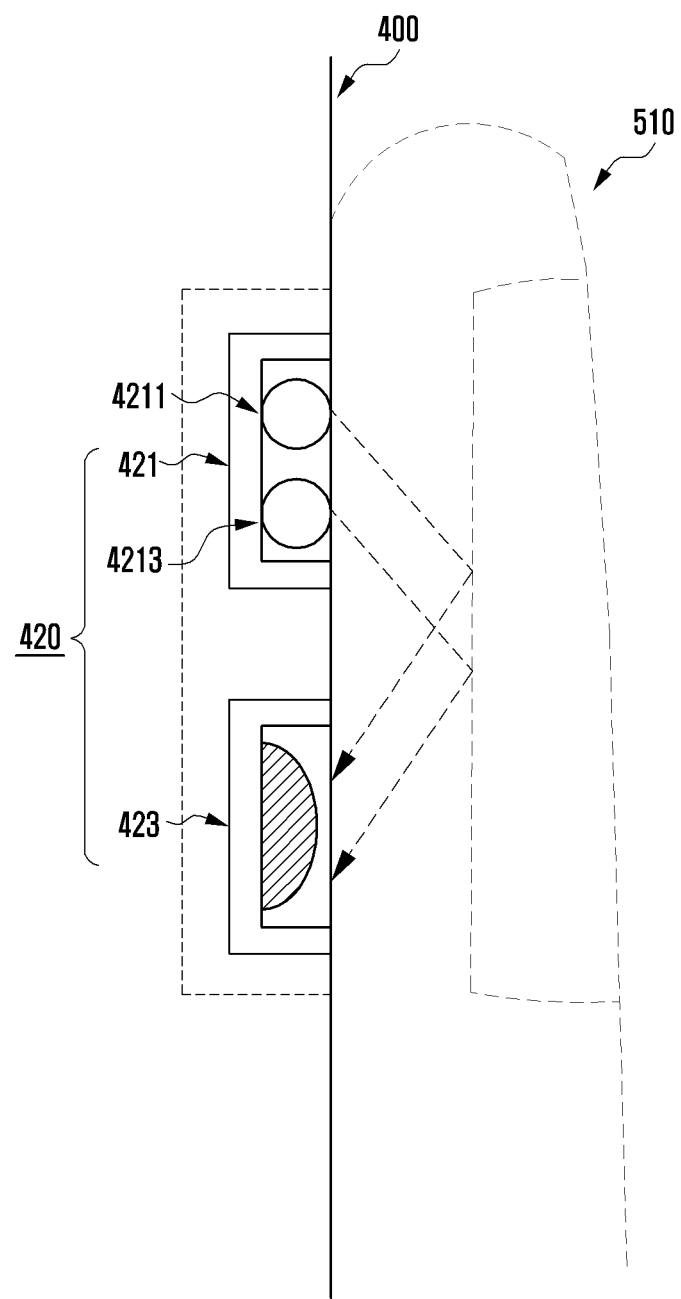
FIGS. 7A and 7B illustrate an operation of a sensor module of an electronic device, according to an embodiment of the present invention.
Figure 7B:
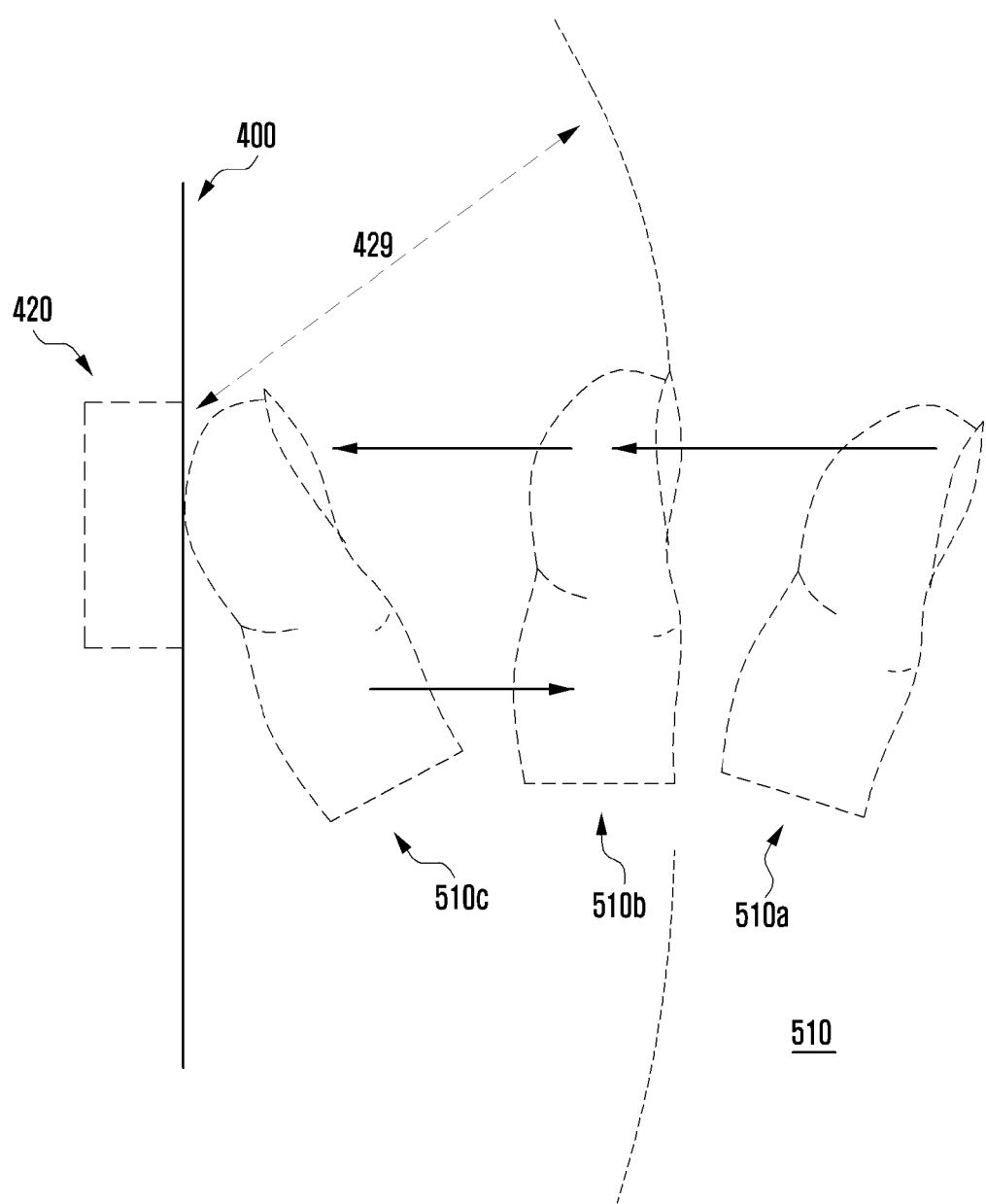

FIGS. 7A and 7B illustrate an operation of a sensor module of an electronic device, according to an embodiment of the present invention.

Referring to FIG. 7A, the sensor module 420 includes the light emitting unit 421 and the light receiving unit 423. The light emitting unit 421 generates an incident light and irradiate the light toward the subject 510 to be examined corresponding to a part of the human tissues, and the light receiving unit 423 receives a reflected light that is generated when the incident light penetrating the subject 510 to be examined is reflected and returned.

The incident light generated from the light emitting unit 421 may be implemented to have a particular wavelength. The incident light may be, for example, a ray indicating a green light. Since the green incident light has a relatively low skin transmittance and high absorption compared to visible lights of other colors, the green incident light may be used for a wearable device worn on the wrist. Further, the incident light may be, for example, a ray indicating a red light.

Alternatively, the light emitting unit 421 may be implemented as one or more LEDs to generate different wavelengths. The one or more LEDs may generate, for example, visible lights of green, red, or other colors or generate an Infrared (IR).

As shown in FIG. 7A, for example, the light emitting unit 421 includes a first light emitting unit 4211 and a second light emitting unit 4213 having different wavelengths. The first light emitting unit 4211 and the second light emitting unit 4213 irradiate incident lights of different wavelengths to the subject 510 to be examined and each of the reflected incident lights is received by the light receiving unit 423.

The sensor module 420 may be configured to include a PPG sensor including the light emitting unit 421 and the light receiving unit 423. As the heart within the human body contracts and relaxes, a blood flow rate of peripheral blood vessel changes and, accordingly, volumes of the peripheral blood vessels also change. The PPG sensor measures a change in the volume of the peripheral blood vessel by detecting a penetration amount of the light irradiated to the subject to be examined, and measures one or more of a change in a blood amount, and blood oxygen saturation within the vessel based on the change in the volume of the peripheral blood vessel. The PPG sensor measures a variation in a time interval between heart rates or heartbeats per unit time based on the measured change in the blood amount within the vessel. Accordingly, the PPG sensor may operate as a Heart Rate Monitor (HRM) which can measure a heart rate based on the measured blood amount information.

The human tissue corresponding to the subject 510 to be examined may be, for example, a finger. While the contact state of the subject 510 on the surface of the sensor module 420 is maintained for a predetermined time after the subject 510 to be examined contacts the surface of the sensor module 420, the sensor module 420 detects a change in the blood amount within the human tissue corresponding to the subject 510 to be examined according to a contraction period and a relaxation period. For example, the sensor module 420 detects a change in brightness since it is relatively dark in the contraction period since the blood amount increases and it is relatively bright in the relaxation period since the blood amount decreases. The measurement module included in the sensor module 420 detects the light reflected from a vessel within the human tissue through the light receiving unit 423 and converts the detected light into an electrical signal, so as to acquire the physiological signal of the subject 510 to be examined. For example, the sensor module 420 converts an amount of the light detected by the light receiving unit 423 into voltage and receives the voltage as an input, and calculates an elapsed time between heart rates or heartbeats based on the measurement of a voltage change period.

The control module 430 analyzes the HRV based on the physiological signal received by the sensor module 420 and acquires physiological information including autonomic nervous system information of the subject 510 to be examined based on a result of the analysis. The analysis is an analysis of a frequency area of the HRV, for example, analysis of power peak information generated in a particular frequency band based on Power Spectrum Density (PSD). The PSD may include a correlation function method, a fast Fourier transform, or an autoregressive technique. The physiological information acquired based on a result of the analysis of the HRV may be information related to immune deficiency, physical stress, physical fatigue, lack of sleep, chronic stress, depression, and emotion (for example, preference, fright, arousal state, etc.).

The control module 430 measures oxygen saturation based on the physiological signal received by the sensor module 420. To this end, the sensor module 420 may include an oxygen saturation sensor, and the oxygen saturation sensor measures a ratio of the hemoglobin saturated with oxygen of the total hemoglobin. The sensor module 420 for measuring the oxygen saturation may include the light emitting unit 421 including a red LED and an IR LED. Since a red wavelength and an IR wavelength have different reaction sensitivities to a change in oxygen saturation of arterial blood, SpO2 is measured through a difference between the sensitivities. Physiological information acquired based on a result of the measurement of SpO2 may be information on burned calories, a difficulty in breathing, clouded consciousness, or a body state during an exercise.

Referring to FIG. 7B, the control module 430 detects an input operation corresponding to a particular movement of the subject 510 to be examined with respect to the surface of the sensor module 420 at least based on the input signal including the physiological signal. The input operation may be distinguished based on a particular area within a particular distance 429 from the surface of the sensor module 420. The particular area may be a detection area in which the sensor module 420 can detect the subject 510 to be examined. Further, the detection area may be an area within a particular range distance from the sensor module 420 so that the physiological signal received by the sensor module 420 can indicate meaningful physiological information.

For example, the detection area may be an area within a distance in which a measurable signal for the subject 510 to be examined can be received or an area in which a signal corresponding to a particular percentage of the intensity of the maximum measurable signal can be received. The control module 430 determines the proximity of the subject 510 to be examined or whether the subject 510 to be examined makes contact based on the input signal including the physiological signal of the subject 510 to be examined. The input operation may include, for example, an approach operation, a contact operation, or a separation operation.

The approach operation is an operation by which the subject 510 to be examined enters the detection area; that is, an operation by which the subject 510a to be examined enters a location of the subject 510b to be examined within the detection area. The contact operation may be an operation by which the subject 510 to be examined contacts at least a part of the surface of the sensor module 420 or an operation by which the subject 510b to be examined moves to a location of the subject 510c to be examined to contact the surface of the sensor module 420. The separation operation may be an operation by which the subject 510 moves away from the surface of the sensor module 420 or an operation by which the subject 510c to be examined separates from the surface of the sensor module 420 and moves to the location of the subject 510b to be examined.

Hereinafter, a method of determining the proximity of the subject to be examined will be described. According to various embodiments described below, the control module 430 may detect an input operation of the subject 510 to be examined by determining whether the subject 510 to be examined enters the detection area based on the input signal including the physiological signal, whether the subject 510 to be examined contacts at least a part of the surface of the sensor module 420, or whether the subject 510 to be examined separates with the surface of the sensor module 420.

When the subject 510 to be examined contacts at least a part of the PPG sensor, the PPG sensor receives the physiological signal including at least one of a DC component and an AC component. The AC component is a signal of a component, which varies relatively quickly depending on the heartbeat due to contraction and relaxation of the heart, and the DC component is a signal of a component, which varies relatively slowly depending on blood volume, and an absorption degree or a reflection degree of the tissues surrounding the vessel regardless of the heartbeat among the physiological signal.

Figure 8A:
FIGS. 8A and 8B are graphs illustrating physiological signals detected by an electronic device according to time lapse, according to an embodiment of the present invention.
Figure 8B:
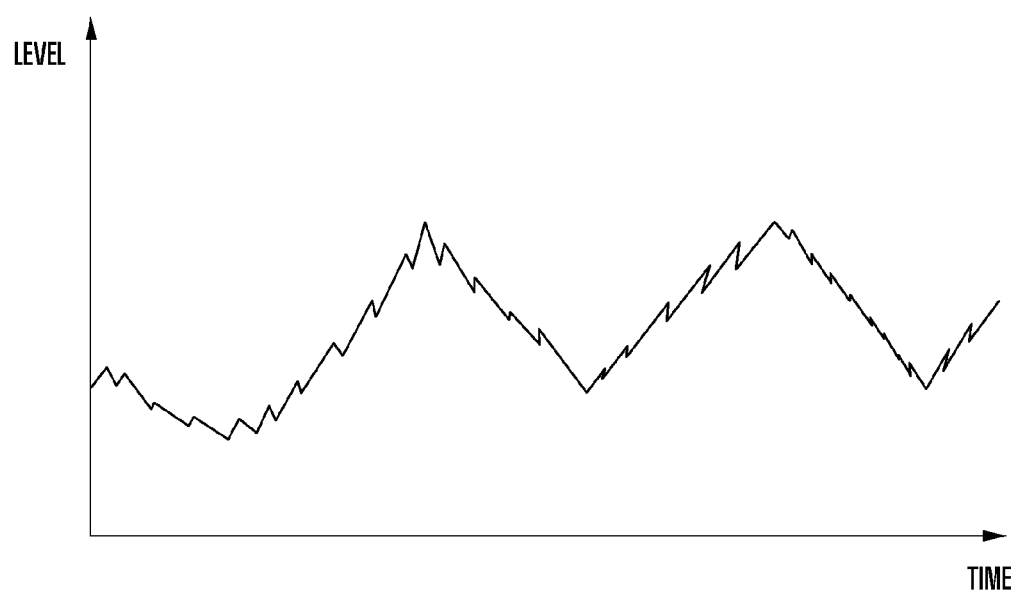

FIGS. 8A and 8B are graphs illustrating physiological signals detected by an electronic device according to time lapse, according to an embodiment of the present invention.

Referring to FIGS. 8A and 8B, the control module 430 determines the proximity of the subject 510 to be examined or whether the subject 510 to be examined contacts, based on at least one of a signal level and a signal pattern of the DC component or the AC component of the physiological signal received by the PPC sensor.

Referring to FIG. 8A, an example of a waveform of the physiological signal including only the DC component is provided.

Referring to FIG. 8B an example of a waveform of the physiological signal including both the DC component and the AC component is provided.

The control module 430 may determine whether the subject 510 to be examined makes contact, based on whether a signal level of the physiological signal is larger than a particular value. The signal level may be a physiological signal value determined based on the DC component or the AC component.

The control module 430 may determine whether the subject 510 to be examined makes contact, based on whether a level value of the DC component of the physiological signal is larger than a particular value.

The control module 430 may determine whether the subject 510 to be examined makes contact, based on whether a level value of the AC component of the physiological signal is within a particular value.

For example, when the level values of the DC component are classified into a first range, a second range, and a third range (first range<second range<third range), the control module 430 determines that the subject 510 to be examined is located outside the detection area when the level value of the DC component corresponding to the physiological signal is in the first range, determines that the subject 510 to be examined is located inside the detection area when the level value of the DC component is in the second range, and determines that the subject 510 to be examined contacts the surface of the sensor module 420 when the level value of the DC component is in the third range.

When detecting the input operation corresponding to the movement based on the physiological signal of the subject 510 to be examined, the control module 430 detects an approach operation when a change from the first range to the second range is detected, a contract operation when a change from the second range to the third range is detected, and a separation operation when a change from the third range to the second range is detected.

In another example, when the level value of the DC component which can be measured through the PPG sensor ranges from 0 to 200,000, the first range is less than or equal to 60,000, the second range is greater than 60,000 and less than 100,000, and the third range is greater than or equal to 100,000.

In another example, compared to the maximum value of the level value of the DC component, the first range may be less than or equal to 30%, the second range may be less than 50%, and the third range may be greater than or equal to 50%.

The level value of the DC component corresponding to the physiological signal may become different through a process of amplifying the received signal. When the subject 510 to be examined is located outside the detection area, the level of the DC component of the physiological signal may become different by an ambient light of the electronic device 400, so that an operation for removing the component by the ambient light is first performed.

The control module 430 may determine the proximity of the subject 510 to be examined or whether the subject 510 to be examined makes contact, based on the signal pattern of the physiological signal. For example, the control module 430 may determine the proximity of the subject 510 to be examined or whether the subject 510 to be examined makes contact, based on an amplitude of the AC component included in the physiological signal. As the amplitude of the AC component of the physiological signal is small, a difference in an increase and a decrease of the light received by the light receiving unit 423 according to vasodilation in the contraction period and vasoconstriction in the relaxation period decreases. In this case, it is determined as a non-contact state or a proximity state rather than the contact state in which the physiological signal of the subject 510 to be examined is sufficiently received.

For example, when the amplitude of the AC component is classified into a first range and a second range, the control module 430 determines that the subject 510 to be examined is located outside the detection area if a maximum or average amplitude change measured using peaks of the AC component included in the physiological signal is in the first range, and determines that the subject 510 to be examined is located inside the detection area if the maximum or average amplitude change is in the second range. In this case, when detecting the input operation corresponding to the movement of the subject 510 to be examined, the control module 430 detects that the input operation corresponds to the approach operation if a change from the first range to the second change is detected. For example, compared to the maximum amplitude of the AC component included in the physiological signal, the first range may be below 20% and the second range may be from 20% to 60%.

According to another embodiment, when detecting the input operation corresponding to the movement of the subject 510 to be examined, the control module 430 detects the contact operation if the amplitude (for example, a peak value) of the AC component included in the physiological signal is larger than or equal to a particular amplitude, and detects the separation operation if the amplitude of the AC component is smaller than the particular amplitude.

When detecting the input operation corresponding to the movement of the subject 510 to be examined, the control module 430 detects the contact operation if a state, in which the amplitude of the peak value of the AC component included in the physiological signal becomes larger than or equal to the particular amplitude, is maintained for a predetermined time or a predetermined number of successive peak values remain in the value larger than or equal to the particular amplitude, and detects the separation operation if a state, in which the amplitude of the peak value becomes smaller than the particular amplitude, is maintained for the predetermined time or the predetermined number of successive peak values remains in the value smaller than the particular amplitude.

When detecting the input operation corresponding to the movement of the subject 510 to be examined, if a DC component included in the physiological signal is close to a maximum reception level value and an AC component included in the physiological signal is very weak, which is equal to or small than a particular level, the control module 430 detects the state in which the subject 510 to be examined is located inside the detection area or the non-contact or proximity state rather than the contact state in which the subject 510 to be examined contacts the surface of the sensor module 420. In this case, the control module 430 determines that an amount of the light received by the light receiving unit 423 included in the sensor module 420 is large but the reflected light or transmitted light of the subject 510 to be examined is not measured.

When the sensor module 420 includes an illumination sensor, the control module 430 determines the proximity of the subject 510 to be examined or whether the subject 510 to be examined makes contact, based on a level of an amount of the light received through the illumination sensor and the physiological signal.

As described in the aforementioned various embodiments, the control module 430 detects the input operation of the subject 510 to be examined corresponding to the movement of the subject 510 to be examined, based on the input signal including the physiological signal.

When a condition for activating the biometric sensor is met, the control module 430 activates the sensor module 420 to include the physiological signal in the input signal. For example, when the camera module 410 is activated, if the face of the subject for photography is detected in a preview image received through the camera module 410, if the proximity of the subject to be examined is detected by the proximity sensor included in the sensor module 420, or if the existence of the subject to be examined is detected through a periodical monitoring by the PPG sensor included in the sensor module 420, the control module 430 considers that the condition for activation is met, and thus activates the biometric sensor. Thereafter, the sensor module 420 receives the input signal including the physiological signal acquired through the activated biometric sensor. While the sensor module 420 receives the input signal including the physiological signal acquired through the activated biometric sensor, the control module 430 may control the audio module 280 to output audio data or control the motor 298 or a haptic module to output tactile feedback or force feedback.

Accordingly, the electronic device performs an operation of receiving the physiological signal of the user through the biometric sensor and an operation of acquiring an image through the camera module of the electronic device at least based on the change in the physiological signal. The change in the physiological signal is detected based on at least one of a level and a pattern of the physiological signal.

Figure 9:
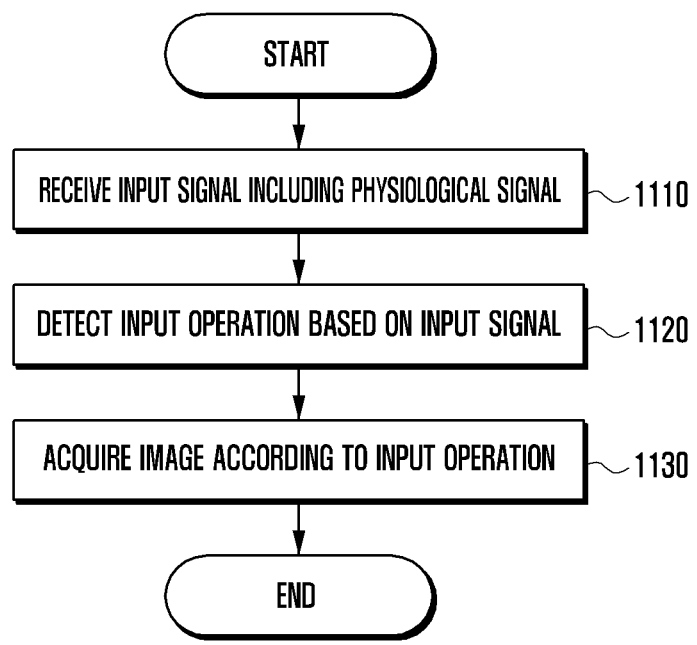
FIG. 9 is a flowchart of an operation for acquiring an image based on an input signal by the electronic device, according to an embodiment of the present invention.

FIG. 9 is a flowchart of an operation for acquiring an image based on an input signal by the electronic device, according to an embodiment of the present invention.

Referring to FIG. 9, the electronic device 400 receives an input signal including a physiological signal, detects an input operation based on the input signal, and controls the camera module 410 according to the input operation.

The sensor module 420 receives an input signal including a physiological signal in step 1110. For example, when the user grasping the electronic device 400 approaches or contacts the sensor module 420, the sensor module 420 acquires the physiological signal from the subject 510 to be examined, which corresponds to a part of the user's body. The sensor module 420 may be a PPG sensor or an ECG sensor, and the physiological signal may be a PPG signal or an ECG signal. The sensor module 420 may further include sensors for measuring a physical quantity related to the electronic device 400. In this case, the sensor module 420 acquires a measurement signal for the physical quantity related to the electronic device 400. The input signal includes the physiological signal and may further include the measurement signal. The measurement signal is a measurement value of another physical quantity (for example, proximity by the illumination sensor) for the part of the user's body.

The control module 430 detects an input operation at least based on the input signal in step 1120. The control module 430 detects an input operation of the subject 510 to be examined based on the physiological signal included in the input signal. Further, the control module 430 detects the input operation of the subject 510 to be examined based on at least one of the physiological signal included in the input signal and another measurement signal. The input operation is detected based on at least one of a signal level or a signal pattern of the input signal.

The input operation detected by the control module 430 may be an approach operation, and the approach operation is an operation by which the subject 510 to be examined enters the detection area from the outside of the detection area.

The input operation detected by the control module 430 may be a contact operation, and the contact operation is an operation by which the subject 510 to be examined contacts at least a part of the surface of the sensor module 420.

The input operation detected by the control module 430 may be a separation operation, and the separation operation is an operation by which the subject 510 to be examined is separated from the surface of the sensor module 420.

The control module 430 acquires an image through the camera module 410 according to the input operation in step 1130. When the input operation is the contact operation, the control module 430 controls the camera module 410 to acquire the image. When the input operation is the separation operation, the control module 430 controls the camera module 410 to acquire the image. When the input operation is the approach operation, the control module 430 controls to change a setting (for example, a focus control or a white balance control) of the camera module 410.

The control module 430 control the camera module 410 to start acquiring the image when the input operation is a first input operation and to end acquiring the image when the input operation is a second input operation. For example, photographing is started by a first contact operation, and the photographing is terminated when a second contact operation is made after the generation of the separation operation. Alternatively, when a multi-touch, that is, two contact operations are generated by different fingers, the image acquisition is started by the contact operation of the first finger and the image acquisition is terminated by the contact operation of the second finger. By the plurality of input operations, a panorama image or a video including a plurality of images may be photographed.

The control module 430 controls the camera module 410 based on one or more input operations detected at least based on the input signal, a time for which each of the input operations is maintained, or sequences of the one or more input operations. Further, the control module 430 changes a setting of the camera module 410 to acquire the image according to the one or more input operations. Hereinafter, various embodiments of this document will describe that the control module 430 controls the camera module 410 at least based on one or more detected input operations.

Alternatively, the control module 430 may control the camera module 410 or the audio module 280 based on one or more detected input operations at least based on a time when the input operation is generated. In this case, the control module 430 performs an operation for continuously acquiring one or more of images or audio data through at least one of the camera module 410 and the audio module 280 and temporarily stores the images or audio data in the memory 230 of the electronic device 400 for a predetermined maintenance time tp (for example, 10 seconds) from the acquisition time. Accordingly, when the input operation is generated, the control module 430 stores one or more of images or audio data from the time (t−tp), which is earlier than the time (t) when the input operation is generated by the predetermined maintenance time, to the time when the input operation is generated.

When the input operation is generated, the control module 430 may acquire and store one or more of images or audio data during a predetermined maintenance time (tn) from the time (t) when the input operation is generated.

Alternatively, the control module 430 store one or more of images or audio data for a time from a time earlier than the time (t) when the input operation is generated by a first maintenance time to a time later than the time (t) when the input operation is generated by a second maintenance time. For example, when the input operation is generated, a sound shot (for example, an operation for recording audio data for a predetermined time including the time before or after the photographing time and correlating the recorded audio data with one or more images) function may be performed.

Figure 10:
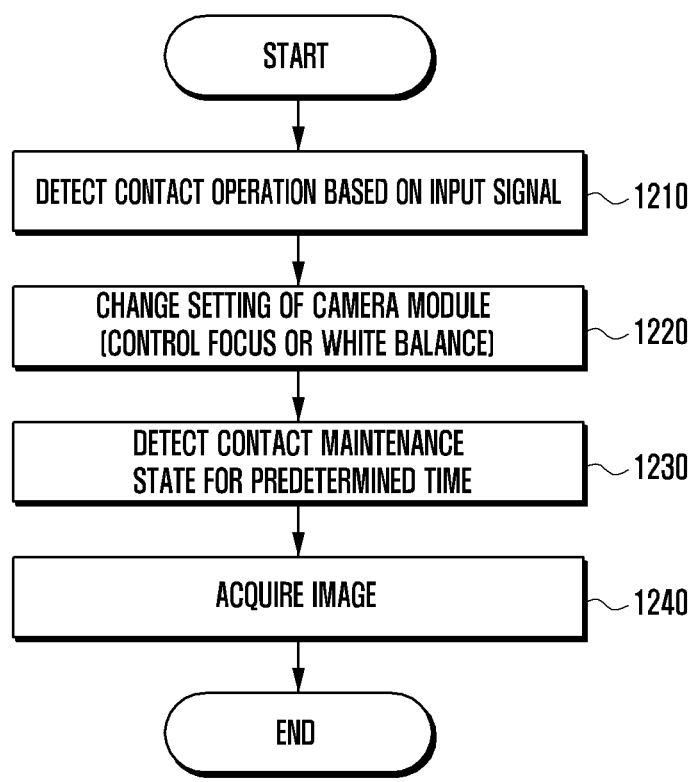
FIG. 10 is a flowchart of an operation for acquiring an image according to a contact operation by the electronic device, according to an embodiment of the present invention.

FIG. 10 is a flowchart of an operation for acquiring an image according to a contact operation by the electronic device, according to an embodiment of the present invention.

Referring to FIG. 10, the electronic device 400 receives an input signal including a physiological signal, such as a user bringing a part of the body including a finger into contact with the sensor module 420 based on the input signal, and, when it is detected that the contact state is maintained for a predetermined time, acquires an image through the camera module after a predetermined time elapses. The control module 430 recognizes the contact operation or the contact maintenance state according to the contact operation as a control command that instructs to perform a preparation operation to acquire the image.

For example, the sensor module 420 receives an input signal including a physiological signal of the subject 510 to be examined, and the control module 430 detects the contact operation at least based on the input signal in step 1210.

When the contact operation is detected, the control module 430 changes a setting of the camera module 410 in preparation for acquiring the image in step 1220. An operation for changing the setting may be an operation for controlling the focus of the camera module 410. Further, the operation for changing the setting may be an operation for controlling white balance of the camera module. The operation for changing the setting may be an operation for controlling at least one of ISO, exposure, aperture, and shutter speed.

The control module 430 detects whether the contact state between the subject 510 to be examined and the sensor module 420 is maintained for a predetermined time after the contact operation at least based on the input signal including the physiological signal in step 1230.

When the contact state between the subject 510 to be examined and the sensor module 420 remains for the predetermined time, the control module 430 acquires the image through the camera module 410 in step 1240.

According to another embodiment, when, after bringing the body part into contact with the sensor module 420 continuously for a predetermined time, the user repeats separation and contact of the body part with respect to the sensor module 420, the control module 430 may acquire the image through the camera module 410 at every contact time. For example, when, after detecting the contact operation at least based on the input signal and detecting that the contact state is maintained for a predetermined time after the contact operation, the control module 430 repeatedly detects the separation operation and the contact operation, the control module 430 may repeatedly acquire the image through the camera module 410 according to the separation operation and the contact operation.

According to another embodiment, when, after maintaining the contact state between the body part and the sensor module 420 for a predetermined time, the user repeats separation and contact of the body part with respect to the sensor module 420, the control module 430 may measure the number of times by which the separation and the contact are repeated and switch to a predetermined setting or mode. For example, when, after detecting the contact operation at least based on the input signal and detecting that the contact state is maintained for a predetermined time after the contact operation, the control module 430 repeatedly detects the separation operation and the contact operation, the control module 430 may switch a camera photographing mode according to the separation operation and the contact operation. For example, when the control module 430 detects the separation after two contacts for a predetermined time, the control module 430 may switch the photographing mode to a night photographing mode.

As another example, when the control module 430 detects the separation after three contacts for a predetermined time, the control module 430 switch the photographing mode to a sports photographing mode.

When an application program for acquiring an image is not executed in the electronic device 400, the control module 430 may execute the application program as the control module 430 detects the contact of the part of the user's body to the sensor module. For example, after detecting the contact operation and executing the application program for acquiring the image, the control module 430 changes a setting of the camera module 410. Thereafter, when the contact state between the subject 510 to be examined and the sensor module 420 remains for the predetermined time, the control module 430 acquires the image through the camera module 410.

Figure 11:
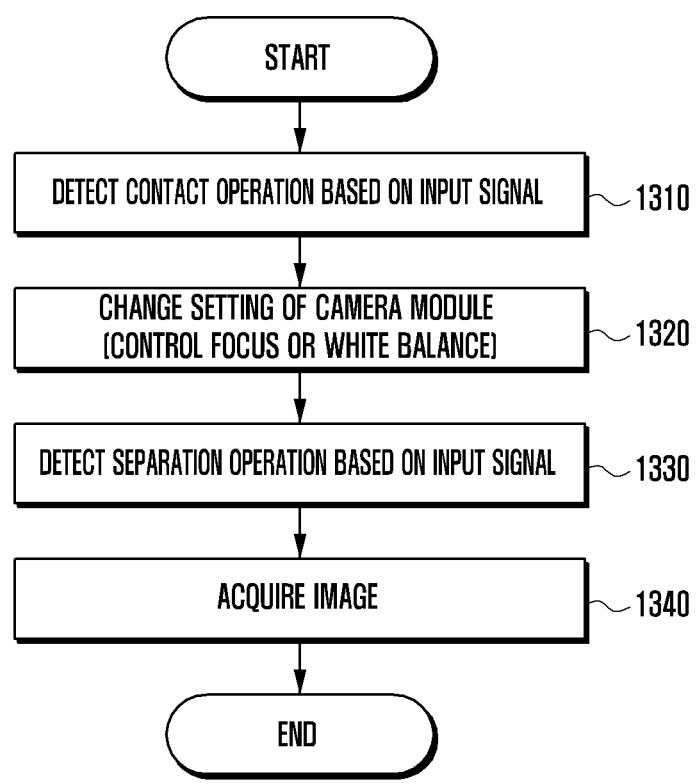
FIG. 11 is a flowchart of an operation for acquiring an image according to a separation operation by the electronic device, according to an embodiment of the present invention.

FIG. 11 is a flowchart of an operation for acquiring an image according to a separation operation by the electronic device, according to an embodiment of the present invention.

Referring to FIG. 11, after the user brings the body part such as a finger into contact with the sensor module based on an input signal including a physiological signal, the electronic device 400 acquires an image through the camera module 410 when the user separates the body part from the sensor module 420.

The sensor module 420 receives an input signal including a physiological signal of the subject 510 to be examined, and the control module 430 detects the contact operation at least based on the input signal in step 1310.

When the contact operation is detected, the control module 430 changes a setting of the camera module 410 as the preparation for acquiring the image in step 1320. An operation for changing the setting may be an operation for controlling the focus of the camera module 410. Further, the operation for changing the setting may be an operation for controlling white balance of the camera module. The operation for changing the setting may be an operation for controlling at least one of ISO, exposure, aperture, and shutter speed.

The control module 430 detects a separation operation by which the subject 510 to be examined is separated from the surface of the sensor module 420 after the contact operation at least based on the input signal including the physiological signal in step 1330.

The control module 430 acquires an image through the camera module 410 according to the detected separation operation in step 1340.

The control module 430 may ignore other photographing commands for acquiring the image except for the detection of the separation operation after the contact operation is detected. For example, the control module 430 may ignore automatic photographing conditions which can be implemented by the electronic device 400, for example, conditions for acquiring the image when a particular pose of the subject for photography included in a preview image is detected, when a smiling face is detected, and when a particular movement pattern is detected, or conditions for acquiring the image when another input signal is received, and may acquire the image only when the separation operation is detected.

Figure 12:
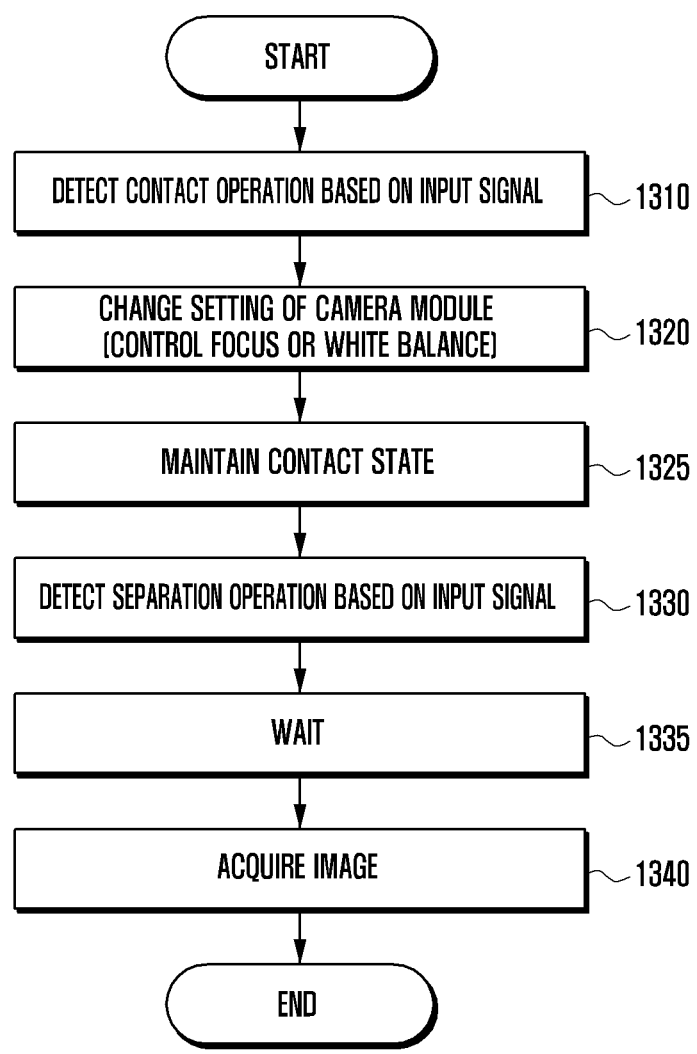
FIG. 12 is a flowchart of an operation for controlling the electronic device, according to an embodiment of the present invention.

FIG. 12 is a flowchart of an operation for controlling the electronic device, according to an embodiment of the present invention.

Referring to FIG. 12, when, after bringing the body part such as a finger into contact with the sensor module 420 based on the input signal including the physiological signal, the user maintains the contact state for a predetermined time, the electronic device 400 may acquire an image through a camera after a waiting time from the separation of the body part from the sensor module by the user.

The sensor module 420 receives an input signal including a physiological signal of the subject 510 to be examined, and the control module 430 detects the contact operation at least based on the input signal in step 1310.

When the contact operation is detected, the control module 430 changes a setting of the camera module 410 in preparation for acquiring the image in step 1320.

The control module 430 determines whether the contact state between the subject 510 to be examined and the sensor module 420 according to the contact operation is maintained for at least a predetermined time in step 1325.

When the control module 430 detects the separation operation by which the subject 510 to be examined is separated from the surface of the sensor module 420 in step 1330, the control module 430 waits until a particular waiting time elapses in step 1335 before acquiring the image in step 1340. The particular waiting time may be determined based on a time for which the contact state is maintained. The control module 430 may display a waiting state on the display 440 for the particular waiting time, for example, in the form of a graphic object.

Figure 13A:
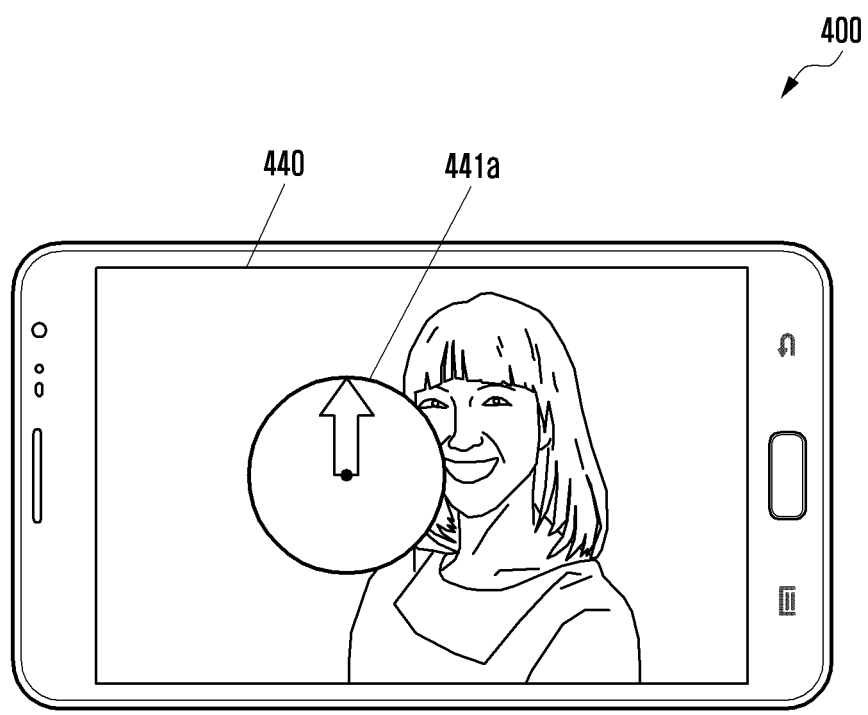
FIGS. 13A and 13B illustrate an elapsing of a particular time, according to an embodiment of the present invention.
Figure 13B:
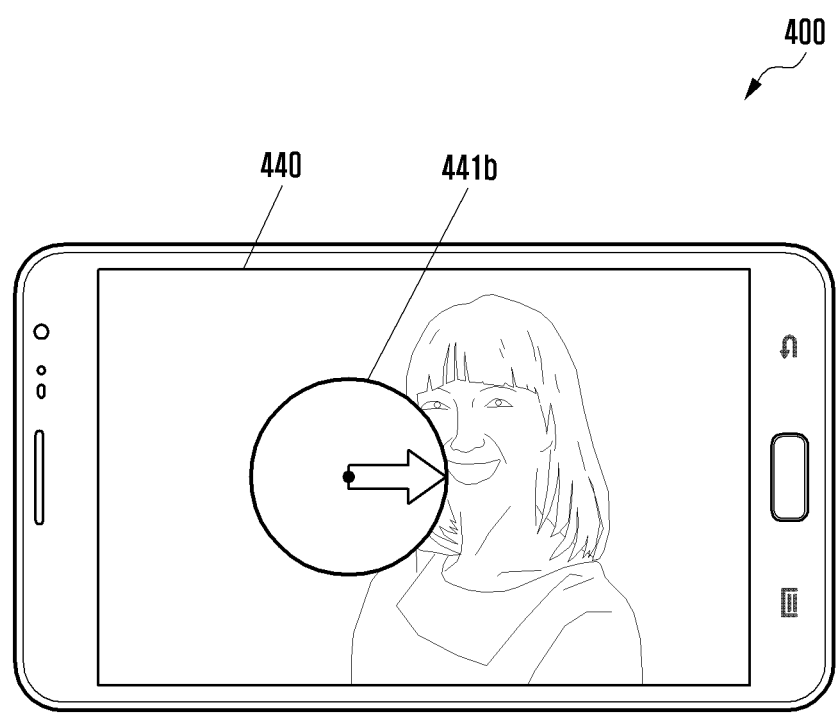

FIGS. 13A and 13B illustrate an elapsing of a particular time, according to an embodiment of the present invention.

Referring to FIGS. 13A and 13B after the detection of the separation operation, the control module 430 displays a graphic object 441a indicating the start of the particular waiting time on the display 440 and then changes the graphic object 441a to a graphic object 441b after the particular waiting time elapses. The control module 430 acquires an image through the camera module 410 after the particular waiting time elapses.

When the image is acquired through the camera module 410, the control module 430 may record a voice for a particular recording time through a microphone included in the electronic device 400. The control module 430 may determine the particular recording time based on the time for which the contact state is maintained. The control module 430 stores the voice together with the image.

FIG. 14 illustrates controlling an electronic device based on a contact sequence, according to an embodiment of the present invention.

Referring to FIG. 14, the sensor module 420 includes the light emitting unit 421 and the light receiving unit 423, and the light emitting unit 421 includes a first light emitting unit 421a and a second light emitting unit 421b having light emitting diodes of different wavelengths. The first light emitting unit 421a may include, for example, LEDs emitting an infrared light, and the second light emitting unit 421b may include, for example, LEDs emitting a red visible light.

When the light emitting unit 421 is implemented as one or more LEDs, the light receiving unit 423 receives reflected lights generated when incident lights of different wavelengths penetrate the subject 510 to be examined and then reflected and returned. The sensor module 420 detects a movement direction of the subject 510 to be examined on the sensor module 420 by detecting contact sequences between the one or more LEDs and the subject 510 to be examined based on the received reflected lights.

The sensor module 420 may generate incident lights from the one or more LEDs simultaneously or at different times. Accordingly, the sensor module 420 detects the activated LED at a particular time among the one or more LEDs and, thus, detects the movement direction of the subject 510 to be examined on the sensor module 420.

The control module 430 detects the movement direction of the subject 510 to be examined at least based on the input signal received through the sensor module 420 including the biometric sensor configured to include one or more LEDs. In this case, the control module 430 controls the electronic device 400 based on the movement direction.

Figure 15B:
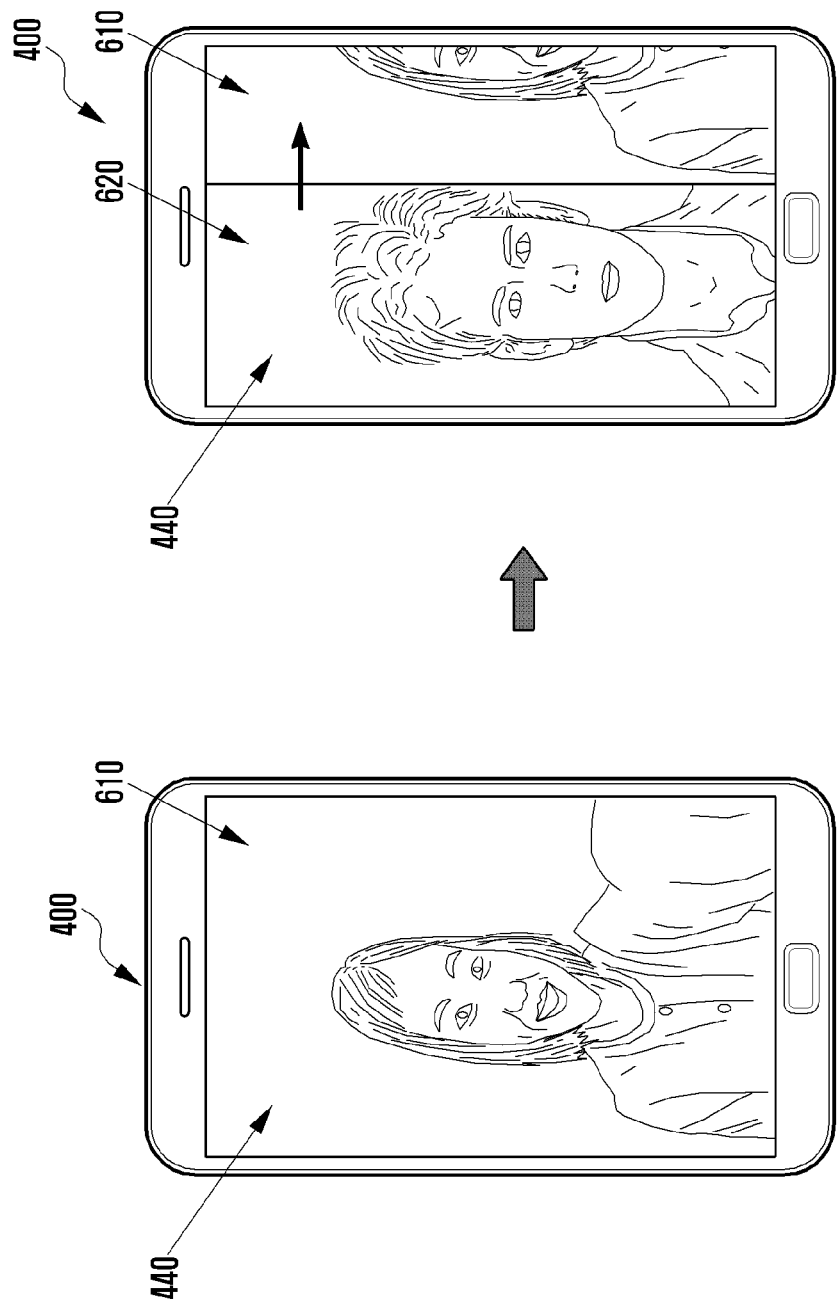

FIGS. 15A and 15B illustrate controlling an electronic device based on a movement direction, according to an embodiment of the present invention.

Referring to FIGS. 15A and 15B after displaying an acquired image 610 on the display 440, the control module 430 detects a movement direction of the subject 510 to be examined from a first location 510a to a second location 510b on the surface of the sensor module 420 disposed on the rear surface of the electronic device 400, moves the image 610 in the movement direction, and displays another image 620 according to the movement of the image. In FIGS. 15A and 15B, the movement direction of the subject 510 to be examined is opposite to the movement direction of the images on the display 440. That is, the movement direction of the subject 510 to be examined, which contacts the sensor module 420 disposed on the rear surface of the electronic device 400 or closely crosses over the sensor module 420, corresponds to a direction from right to left, and the movement direction of the image 620 on the display 440 disposed on the front surface of the electronic device 400 corresponds to a direction from left to right. Further, a speed of contents, which moves on the display 440, may vary depending on a movement speed of the subject 510 to be examined.

The control module 430 moves the content while displaying the content on the display 440 by controlling the electronic device 400 based on the movement direction. For example, the contents may be a webpage, and the movement operation may be a scroll operation. As another example, the contents may be one or more pages of an electronic book, and the movement operation may be a page turn effect operation of the electronic book. As yet another example, the contents may be a menu focus (for example, highlight, cursor, or selection indication) displayed on a menu, and the movement operation may be a movement operation of the menu focus.

Figure 16:
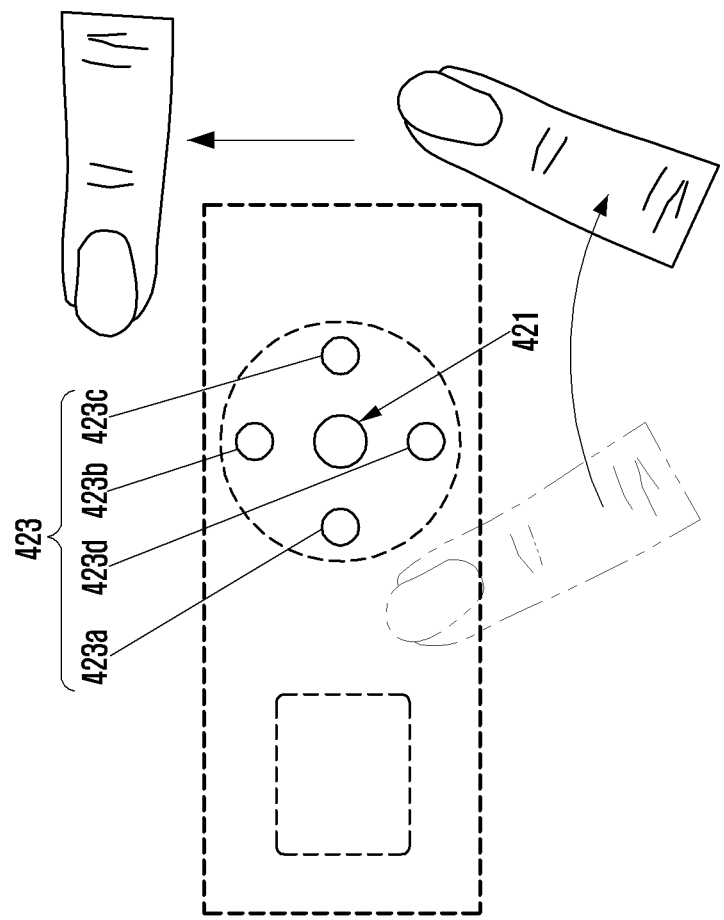
FIG. 16 illustrates controlling an electronic device based on a contact sequence, according to an embodiment of the present invention.

FIG. 16 illustrates controlling an electronic device based on a contact sequence, according to an embodiment of the present invention.

Referring to FIG. 16, the sensor module 420 includes the light emitting unit 421 and the light receiving unit 423, and the light receiving unit 423 may include one or more light receiving diodes, such as a first light receiving diode 423a, a second light receiving diode 423b, a third light receiving diode 423c, and a fourth light receiving diode 423d. In this case, an incident light generated by the light emitting unit 421 is reflected after penetrating the subject 510 to be examined and is received through each light receiving diode. The control module 430 detects a direction of the movement of the subject to be examined on the sensor module 420 based on positions of the one or more light receiving diodes and a difference or a change in the physiological signal received by each light receiving diode.

When the light receiving unit 423 includes two or more light receiving diodes a arranged on left and right sides from the center of the light emitting unit 421, the control module 430 detects left and right movement directions of the subject 510 to be examined on the sensor module 420.

When, the light receiving unit 423 includes four light receiving diodes, for example, the first light receiving diode 423a, the second light receiving diode 423b, the third light receiving diode 423c, and the fourth light receiving diode 423d, the four light receiving diodes are arranged on the top, bottom, left, and right sides from the center of the light emitting unit 421, respectively. In this case, the control module 430 detects left and right movement directions or top, bottom, left, and right movement directions of the subject 510 to be examined on the sensor module 420.

The number of light receiving diodes according to the above described embodiment is only an example, and the light receiving unit 423 may include a different number of light receiving diodes.

The control module 430 may detect the movement direction of the subject 510 to be examined at least based on the input signal received through the sensor module 420 including the biometric sensor configured to include one or more light receiving diodes. In this case, the control module 430 controls the electronic device 400 based on the movement direction as described above.

Figure 17:
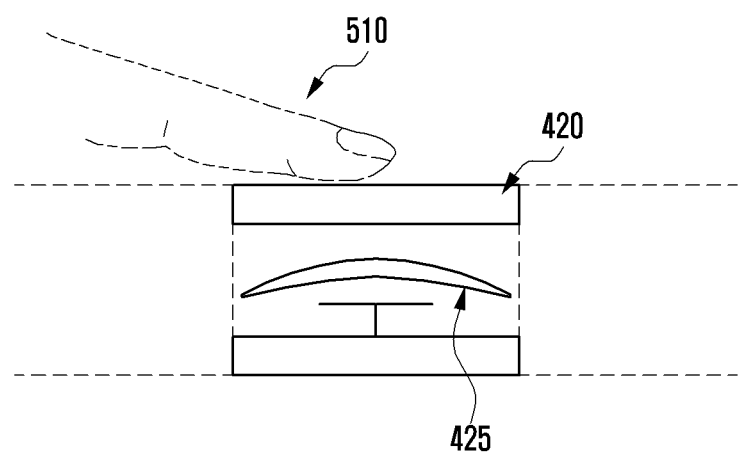
FIG. 17 illustrates a biometric sensor coupled to a button of an electronic device, according to an embodiment of the present invention.

FIG. 17 illustrates a biometric sensor coupled to a button of an electronic device, according to an embodiment of the present invention.

Referring to FIG. 17, the sensor module 420 may be formed to cover a switch disposed on the body of the electronic device 400. The sensor module 420 includes a biometric sensor arranged above a button 425 that covers the switch in an accumulated form. The button 425 and the sensor module 420 may be functionally connected to control image acquisition through the camera module 410. For example, when the sensor module 420 is formed to be disposed above the button 425, the user contacts the sensor module 420 before pressing the button 425, so that the sensor module 420 receives a physiological signal of a user's body part (for example, finger) corresponding to the subject 510 to be examined. In this case, the control module 430 detects an input operation at least based on an input signal including the physiological signal and, accordingly, controls the electronic device 400 based on the input operation, a result of the determination on whether the switch opens or shuts, or both the input operation and the result of the determination on whether the switch opens or shuts.

The electronic device 400 may include sensors for measuring other physical quantities between the sensor module 420 and the button 425, above the sensor module 420, or below the button 425. Although it has been described that the button 425 is formed on the front case of the electronic device 400, the button 425 may be disposed on another surface of the electronic device 400.

Figure 18:
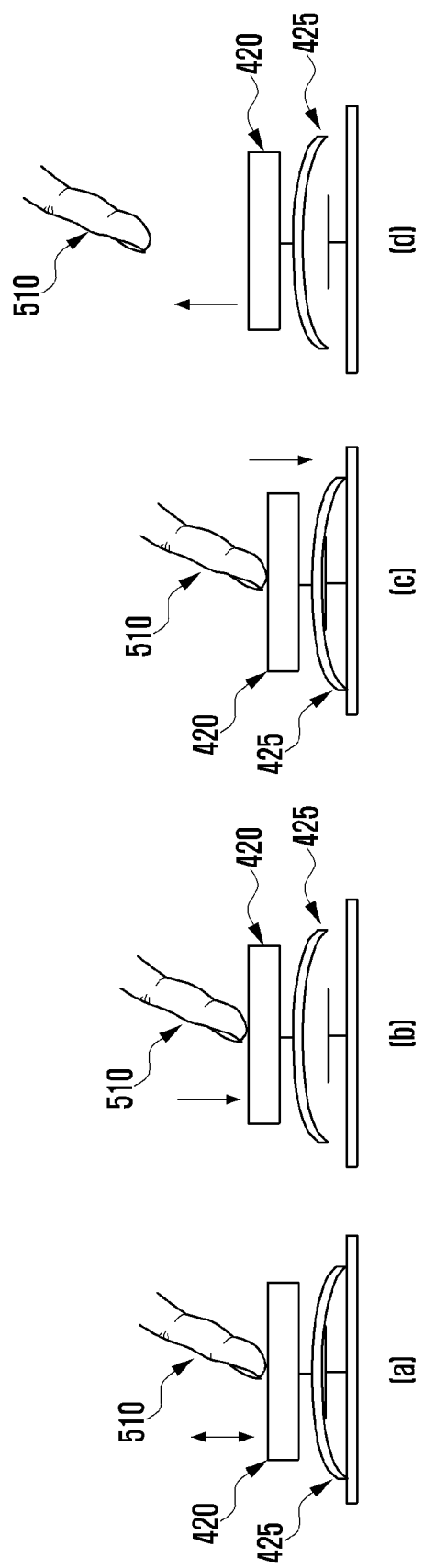
FIG. 18 illustrates a method of using a biometric sensor coupled to a button of an electronic device, according to an embodiment of the present invention.

FIG. 18 illustrates a method of using a biometric sensor coupled to a button of an electronic device, according to an embodiment of the present invention.

Referring to FIG. 18, an electronic device 400 including the sensor module 420 formed to cover the button 425 is provided.

When the biometric sensor included in the sensor module 420 is deactivated, the control module 430 activates the biometric sensor after detecting the press of a button 425 as shown in step [a]. Further, the control module 430 may execute an application program for acquiring an image through the camera module 410 according to the activation of the biometric sensor.

When the control module 430 detects a contact operation or a separation operation of the subject 510 to be examined at least based on the input signal received through the sensor module 420 and detects the press of the button 425 after the contact operation, the control module 430 changes a setting of the camera module 410, as shown in step [b]. For example, the control module 430 may control the focus or white balance according to the contact operation even before the press of the button 425 is detected. The contact operation may correspond to a half-press to focus for controlling the focus of the camera module 410.

Thereafter, as shown in step [c], the control module 430 acquires the image through the camera module 410 according to the press of the switch 452. The control module 430 deactivates the biometric sensor according to the separation operation, as shown in step [d].

Figure 19:
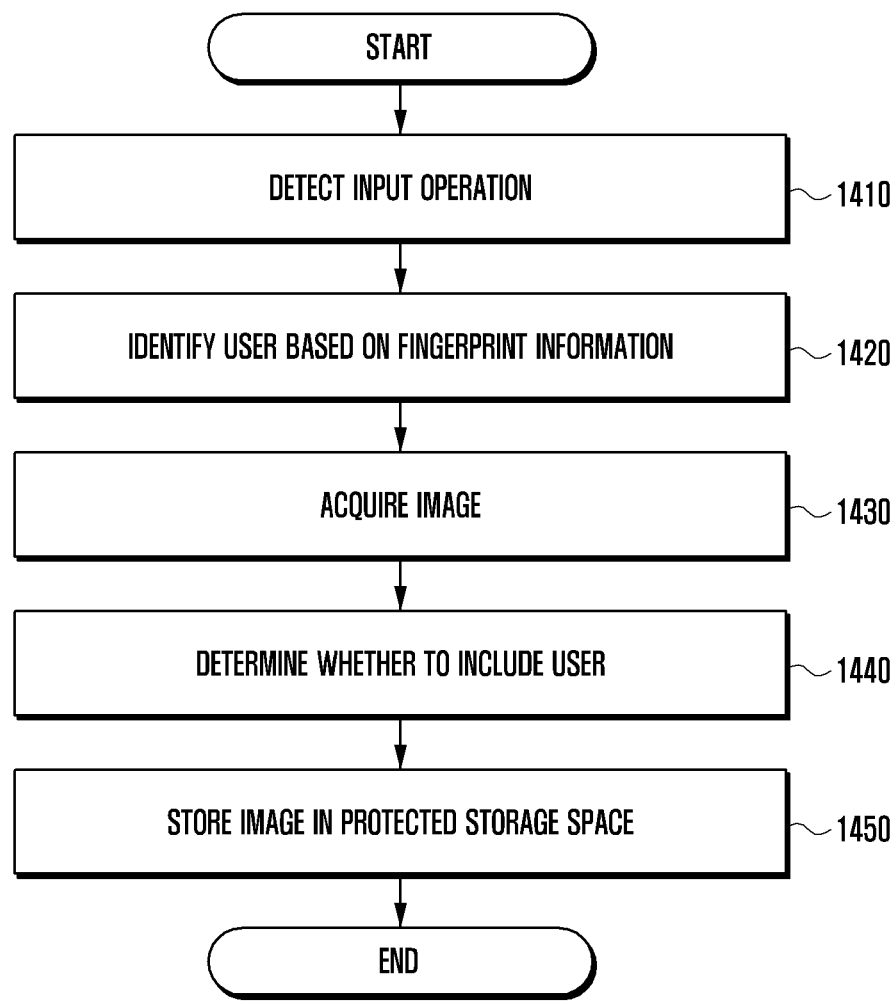
FIG. 19 is a flowchart of an operation for processing an image by using fingerprint information, according to an embodiment of the present invention.

FIG. 19 is a flowchart of an operation for processing an image by using fingerprint information, according to an embodiment of the present invention.

Referring to FIG. 19, the sensor module 420 may include a fingerprint recognition sensor. In this case, the sensor module 420 receives an input signal including information on the fingerprint of the subject 510 to be examined, through the fingerprint recognition sensor. The control module 430 controls the electronic device 400 based on the fingerprint information.

The sensor module 420 receives an input signal including a physiological signal and fingerprint information, and the control module 430 detects an input operation at least based on the input signal in step 1410.

The control module 430 identifies the user based on the fingerprint information included in the input signal in step 1420.

The control module 430 acquires an image through the camera module 410 according to the input operation in step 1430.

The control module 430 detects whether the user is included in the image in step 1440, and, when the user is included in the image, stores the image in a protected storage space in step 1450. The protected storage space may be a secure area existing within the electronic device 400, a personal storage space for the user, a personal storage area based on an external device of the electronic device 400, or a service.

When the fingerprint is determined as the fingerprint of the user who is not identified, the control module 430 may acquire an image through the camera module 410 according to the input operation, and store the image in a guest storage space. The guest storage space may be a published area existing within the electronic device 400 (for example, a memory which can be accessed without user authentication), or a personal storage area based on a service, an internal, or external device of the electronic device 400 storing at least one of the fingerprint information or the image to record the user when the electronic device 400 is stolen.

When the physiological information acquired through the sensor module 420 is heart rate information, the control module 430 may control the electronic device 400 to process the image by using the heart rate information. The electronic device 400 may acquire heart rate information of the subject 510 to be examined at least based on the physiological signal acquired through the sensor module 420. The control module 430 may display the heart rate information on the display 440 together with the image of the user corresponding to the subject 510 to be examined.

Figure 20:
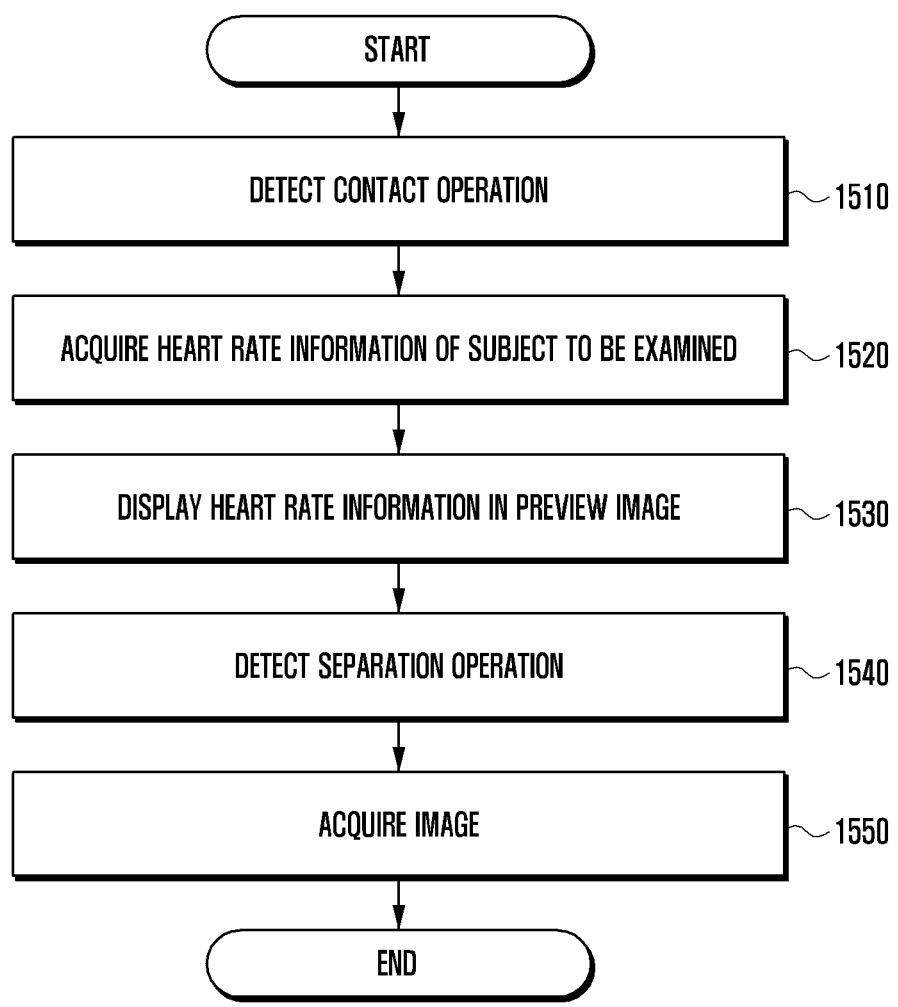
FIG. 20 is a flowchart of an operation for providing a preview image by using heart rate information, according to an embodiment of the present invention.

FIG. 20 is a flowchart of an operation for providing a preview image using heart rate information, according to an embodiment of the present invention.

Figure 21:
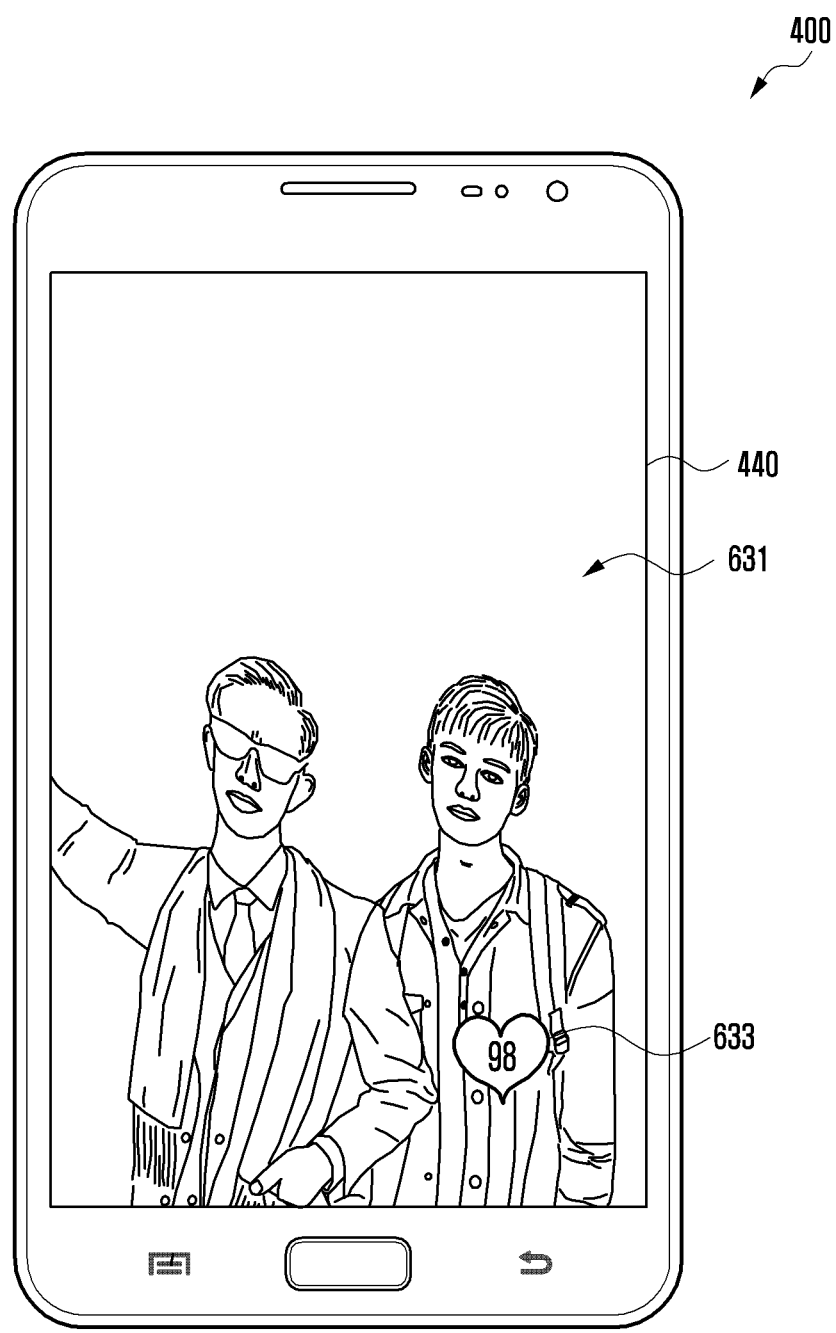
FIG. 21 illustrates a screen displaying a preview image provided using heart rate information, according to an embodiment of the present invention.

FIG. 21 illustrates a screen displaying a preview image provided using heart rate information, according to an embodiment of the present invention.

Referring to FIGS. 20 and 21 the sensor module 420 receives an input signal including a physiological signal of the subject 510 to be examined, and the control module 430 detects a contact operation as an input operation at least based on the input signal in step 1510.

The control module 430 acquires the heart rate information of the subject 510 to be examined at least based on the physiological signal while the contact operation is maintained in step 1520.

The control module 430 displays a preview image 631 acquired through the camera module 410 on the display 440 and also displays heart rate information 633 together with the preview image in step 1530.

The control module 430 detects a separation operation during a contact state in step 1540, and acquire the image by controlling the camera module 410 in step 1550.

The control module 430 may store the image such that the heart rate information is included in the image.

The control module 430 may detect the image of the user corresponding to the subject 510 to be examined included in the preview image and display the image of the user and the heart rate information such that the image of the user and the heart rate information are correlated to each other.

An operation for designating one or more display attributes (for example, a location, size, color, shape, icon, avatar, and predetermined template) of the heart rate information 633 while the preview image 631 is displayed may be further included.

The heart rate information may be information related to stress or emotion determined based on the physiological signal collected through the HRM sensor or the HRV sensor, and display attributes of the heart rate information 633 may be designated or changed based on information on the corresponding stress or emotion.

Figure 22:
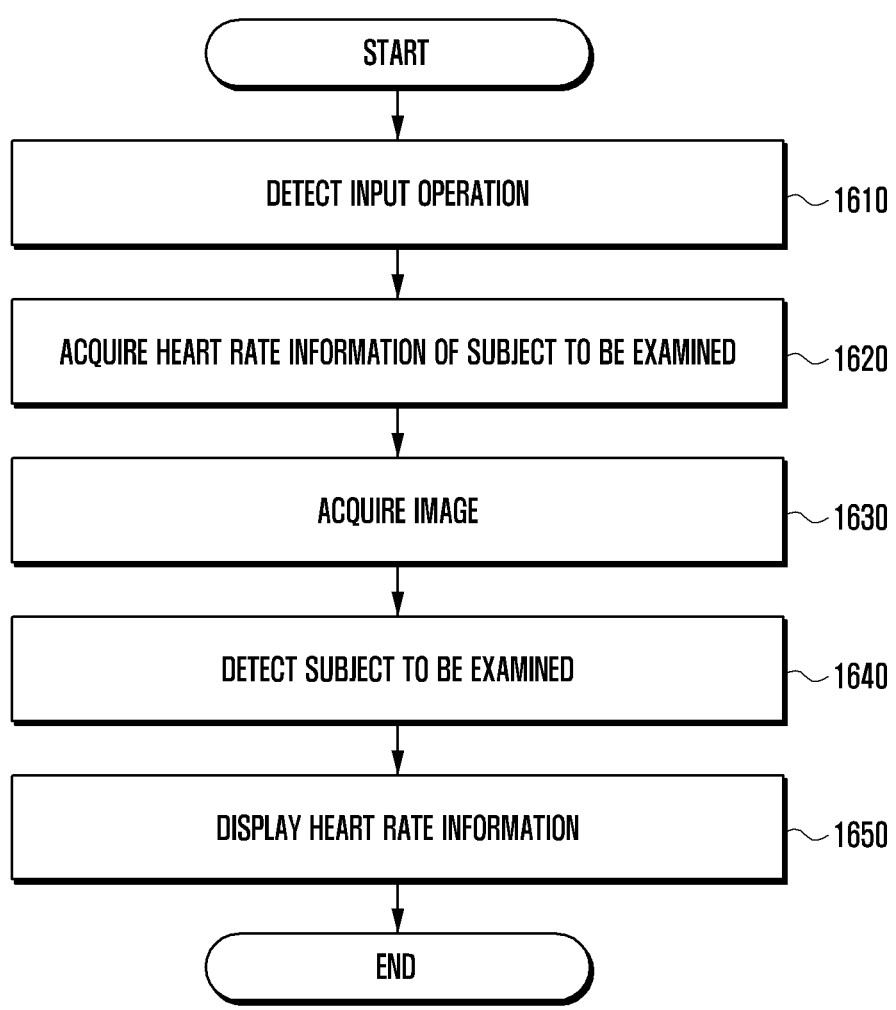
FIG. 22 is a flowchart of an operation for displaying a user image and heart rate information together, according to an embodiment of the present invention.

FIG. 22 is a flowchart of an operation for displaying a user image and heart rate information together, according to an embodiment of the present invention.

Figure 23:
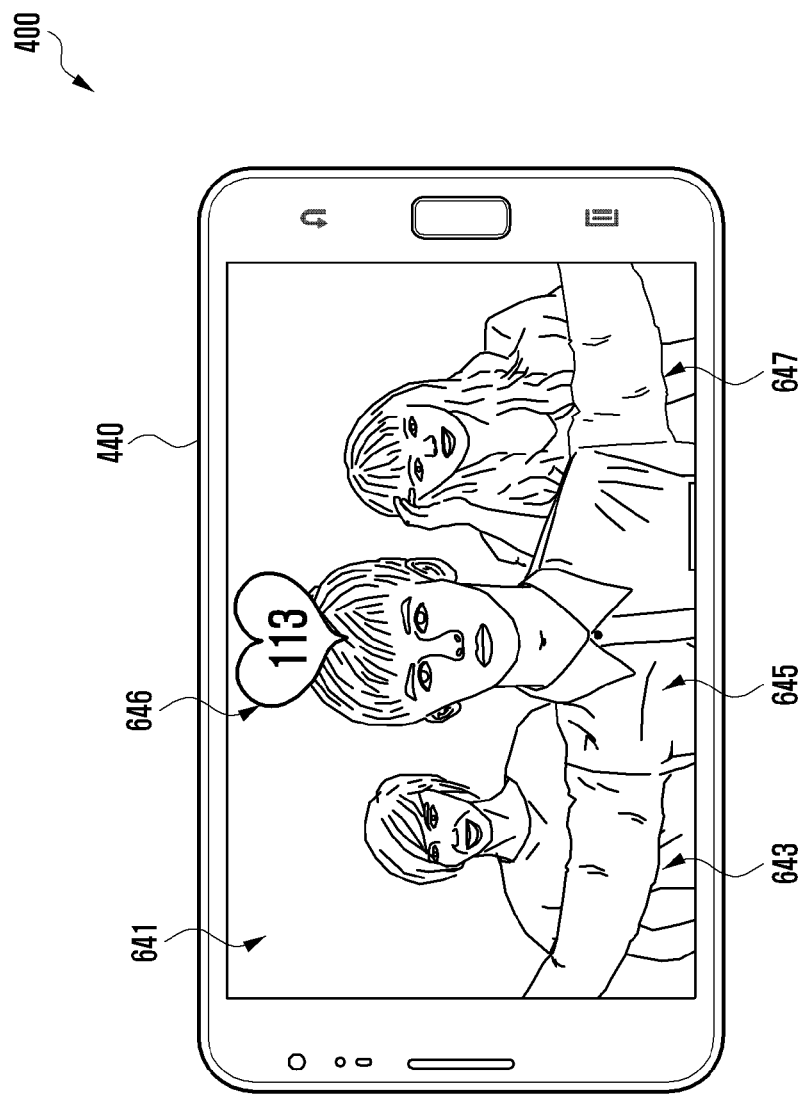
FIG. 23 illustrates a screen displaying an image together with heart rate information, according to an embodiment of the present invention.

FIG. 23 illustrates a screen displaying an image together with heart rate information, according to an embodiment of the present invention.

Referring to FIGS. 22 and 23, for example, the sensor module 420 receives an input signal including a physiological signal of the subject 510 to be examined, and the control module 430 detects an input operation at least based on the input signal in step 1610.

The control module 430 acquires heart rate information of the subject 510 to be examined at least based on the physiological signal in step 1620.

The control module 430 acquires an image through the camera module 410 according to the input operation in step 1630.

The control module 430 detects, within the image, a user image corresponding to the subject 510 to be examined in step 1640. When images of a plurality of people 643, 645, and 647 are included in the image, the control module 430 detects the user image corresponding to the subject 510 to be examined according to the heart rate information, physiological information, or a user setting. The electronic device 400 may include a database including the user image corresponding to the heart rate information, and the user image may be detected based on the database.

The control module 430 displays the acquired image 641 on the display 440 and displays the heart rate information such that the heart rate information is correlated to the user image 645 in a graphic object or text form 646 in step 1650.

The control module 430 may display emotional information based on the physiological information together with the image.

Figure 24:
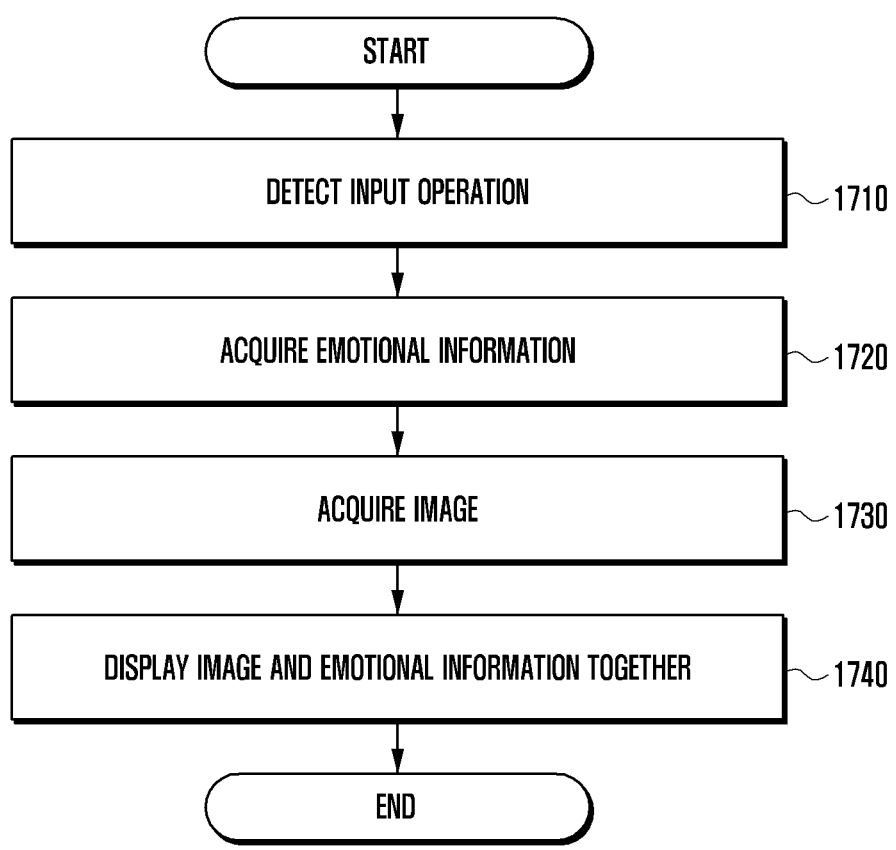
FIG. 24 is a flowchart of an operation for displaying an acquired image and emotional information together, according to an embodiment of the present invention.

FIG. 24 is a flowchart of an operation for displaying an acquired image and emotional information together, according to an embodiment of the present invention.

Figure 25:
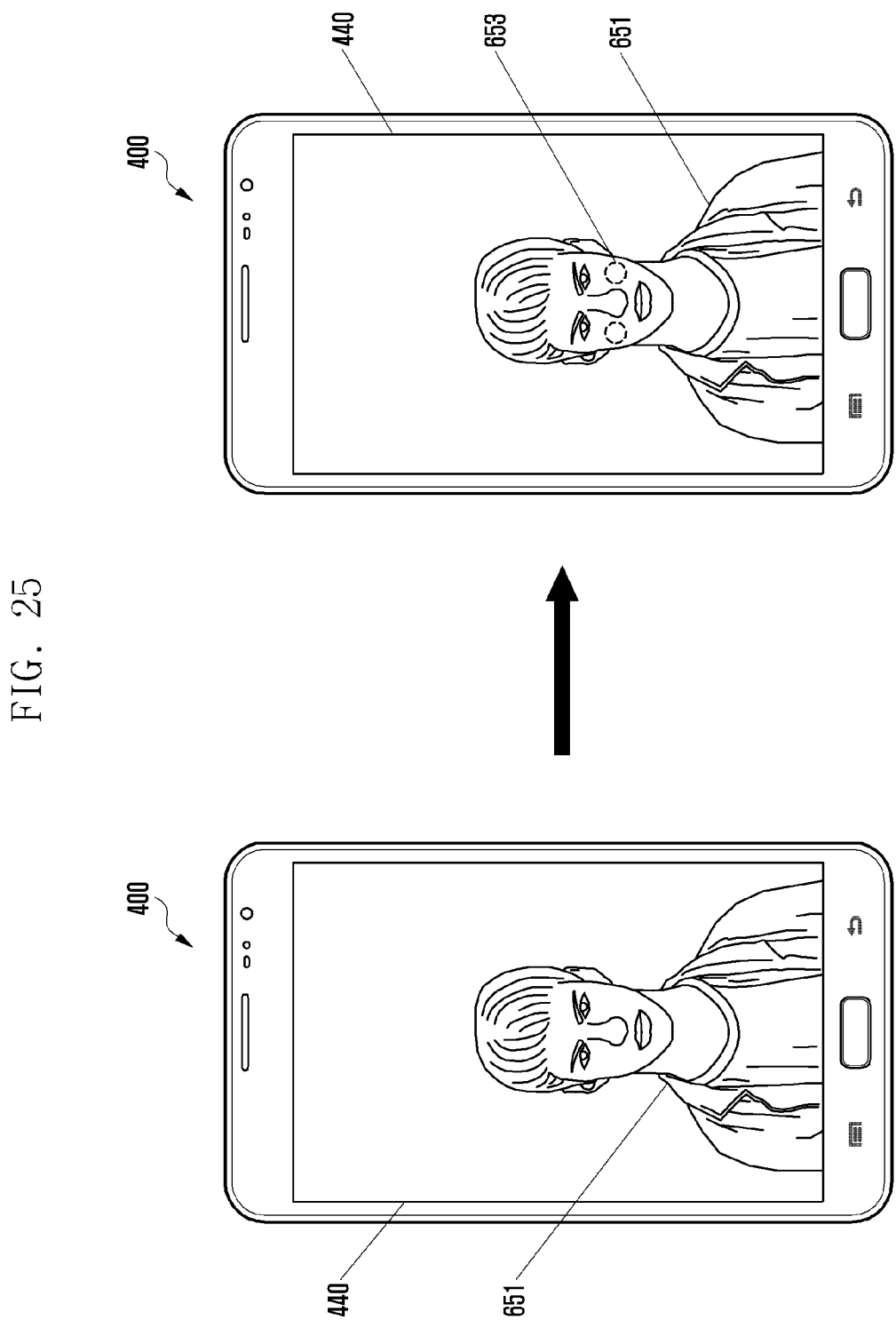
FIG. 25 illustrates a screen displaying an image together emotional information, according to an embodiment of the present invention.

FIG. 25 illustrates a screen displaying an image together emotional information, according to an embodiment of the present invention.

Referring to FIGS. 24 and 25 the sensor module 420 receives an input signal including a physiological signal of the subject 510 to be examined, and the control module 430 detects an input operation at least based on the input signal in step 1710.

The control module 430 acquires emotional information of the subject 510 to be examined at least based on the physiological signal in step 1720. The emotional information may include, for example, joy, shyness, sorrow, or excitement. The emotional information may be acquired based on heart rate information.

The control module 430 determines that the emotional information corresponds to joy by detecting an increase in the heart rate for a predetermined time or a particular pattern of the heart rate signal.

Alternatively, the control module 430 may acquire the emotional information by identifying an emotional state shown in the preview image acquired through the camera module 410. For example, the control module 430 may acquire the emotional information based on at least one of a movement pattern of the user's body within the preview image, a facial expression in a face image, a face shape, a movement pattern of the face (for example, a change in shape of the eyes or mouth), existence or nonexistence of laughter, and existence or nonexistence of blinking.

Further, the control module 430 acquires an image through the camera module 410 according to the input operation in step 1730.

The control module 430 displays the emotional information on the display 440 together with the image in step 1740.

The control module 430 may change the user's facial expression shown in the image according to the emotional information. More specifically, the control module 430 may analyze feature points of the user's face and change a location of a feature point associated with the emotional information among the feature points. When the emotional information corresponds to joy, the control module 430 may change the user's facial expression by changing locations of the feature points corresponding to the mouth such that the mouth corner lifts or lips part, so as to represent the user's smiling face in the image.

The control module 430 may change a part of all of the colors of the user's face shown in the image according to the emotional information. For example, when the emotional information corresponds to excitement or shyness, the control module 430 may make a red color 653 appear on the cheek of the face of the user 651 shown in the image.

The control module 430 may identify people included in the image, acquire physiological information or emotional information of the user corresponding to the subject 510 to be examined and other people, and display the physiological information and emotional information together. To this end, the electronic device 400 can communicate with another device including physiological information of the identified people. The control module 430 may acquire the physiological information of the user based on the physiological signal included in the input signal received through the sensor module 420 and acquire the physiological information of other people through communication with another electronic device corresponding to face recognition information.

Figure 26:
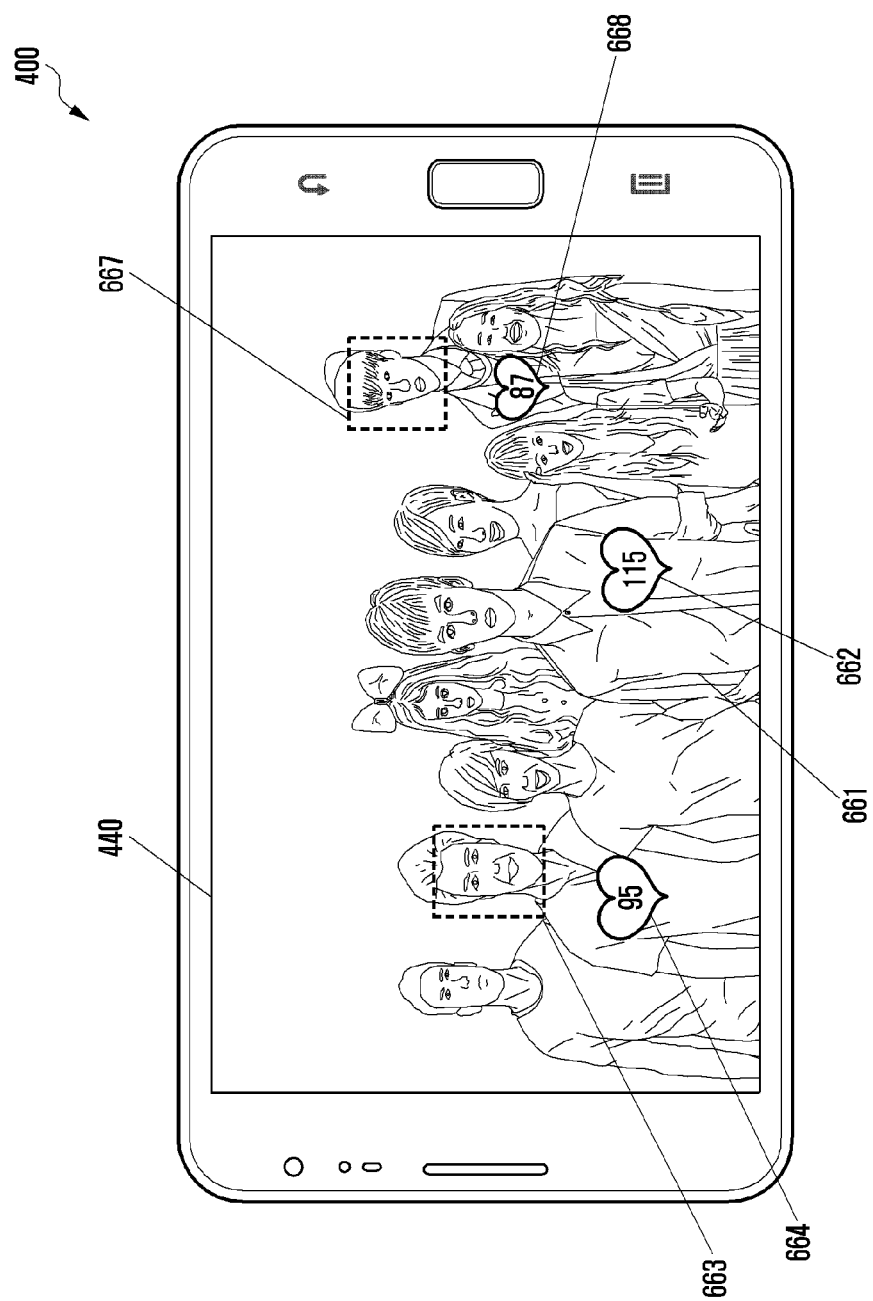
FIG. 26 illustrates a screen displaying an image in which physiological information is correlated with the user, according to an embodiment of the present invention.

FIG. 26 illustrates a screen displaying an image in which physiological information is correlated with the user, according to an embodiment of the present invention Referring to FIG. 26, for example, physiological information 662 of the user 661 corresponding to the subject 510 to be examined is acquired through the sensor module of the electronic device 400 and correlated to the user 661. Further, physiological information 664 and 668 of other users 663 and 667 may be acquired through communication or wearable devices of the other users 663 and 667 and correlated to the other users 663 and 667.

The control module 430 may store physiological information or emotional information together with the image acquired through the camera module 410. The physiological information or the emotional information may be stored in a meta information area of a file format for the image.

FIGS. 27A to 27D illustrate a method of controlling an electronic device to photograph a panorama image, according to an embodiment of the present invention.

Referring to FIGS. 27A to 27D, the sensor module 420 receives an input signal including a physiological signal of the subject 510 to be examined, and the control module 430 detects the input operation at least based on the input signal. The control module 430 combines one or more images acquired according to the detected input operation to generate connected images, for example, panorama images.

When the contact operation is detected, the control module 430 of the electronic device 400 acquires a reference image through the camera module 410 and acquires one or more images connected to the reference image according to up and bottom or left and right rotation of the body of the electronic device 400. The control module 430 displays a guide for indicating locations of the one or more images connected to the reference image according to the rotation of the body on the display of the electronic device 400. The guide displays a photographing direction or a photographing location. When another input operation is detected, the control module 430 combines the reference image and the one or more images. For example, the combination may correspond to a combination of the one or more images corresponding to images above or below the reference image according to the top and bottom rotation of the body or a combination of the one or more images corresponding to images on the left or right side of the reference image according to the left and right rotation of the body. The other input operation may be another contact operation or separation operation.

Referring to FIG. 27A, when the contact operation with respect to the sensor module 420 arranged on the rear surface of the body of the electronic device 400 is detected, the control module 430 acquires a reference image 670*a* through the camera module 411 arranged on the front surface of the body of the electronic device 400. The reference image 670*a* may include an image 671 corresponding to the user of the electronic device 400.

Figure 27B:
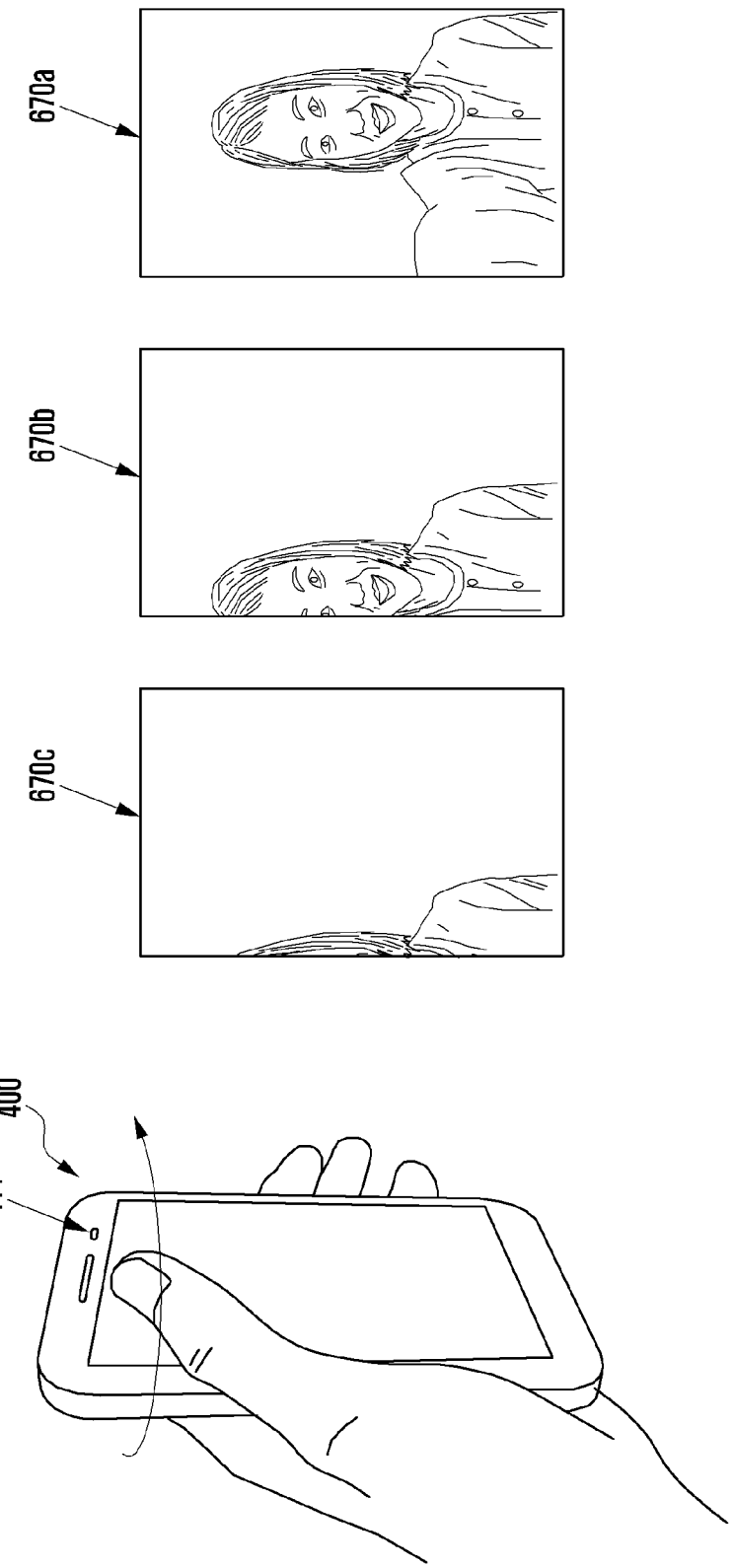

Referring to FIG. 27B, the control module 430 acquires at least one image 670*b* or 670*c* corresponding to an image on the right side of the reference image 670*a* through the camera module 411 as the body of the electronic device 400 rotates counterclockwise. At least one image 670*b* or 670*c* may include at least some areas of the reference image 670*a*.

Referring to FIG. 27C, the control module 430 acquires at least one image 670*d* or 670*e* corresponding to an image on the left side of the reference image 670*a* through the camera module 411 as the body of the electronic device 400 rotates clockwise. At least one image 670*d* or 670*e* may include at least some areas of the reference image 670*a*.

Figure 27D:

Referring to FIG. 27D, when an additional contact operation is detected or when a separation operation is detected after a contact state according to the contact operation is maintained for a particular time, the control module 430 generates one image 670*f* by connecting the reference image 670*a* and at least one image 670*b*, 670*c*, 670*d*, or 670*e*.

Further, the embodiments disclosed in this document are only for the description and understanding of technical contents and do not limit the scope of the present invention. Accordingly, it should be understood by those skilled in the art to which the present invention pertains that various changes in form and details may be made therein without departing from the spirit and scope of the present invention. Therefore, the scope of the present invention is defined not by the detailed description of the present invention, but by the appended claims and their equivalents, and thus, all differences within the scope will be construed as being included in the present invention.

What is claimed is:

1. A method of controlling an electronic device, the method comprising:
   receiving an input signal including a physiological signal of a subject to be examined through a sensor module of the electronic device;
   detecting an input operation based on at least the input signal; and
   acquiring an image through a camera module according to the input operation.

2. The method of claim 1, wherein the physiological signal includes a Photoplethysmography (PPG) measurement signal.

3. The method of claim 1, wherein detecting the input operation comprises detecting a contact operation including contacting at least a part of a surface of the sensor module.

4. The method of claim 1, wherein the input operation is detected based on one of the physiological signal received through the sensor module and a signal level or a signal pattern of another input signal.

5. The method of claim 1, wherein detecting the input operation comprises:
detecting a contact operation including a contact on at least a part of a surface of the sensor module; and
detecting a state in which the contact is maintained for a predetermined time after the contact operation;
and
wherein acquiring the image comprises:
changing a setting of the camera module according to the contact operation; and
acquiring the image through the camera module when the predetermined time elapses.

6. The method of claim 5, wherein changing the setting comprises controlling a focus of the camera module or controlling a white balance of the camera module.

7. The method of claim 1, wherein detecting the input operation comprises detecting an approach operation including approaching a surface of the sensor module within a particular range; and
wherein acquiring the image comprises changing a setting of the camera module according to the approach operation.

8. The method of claim 1, wherein detecting the input operation comprises detecting a separation operation including being separated from a surface of the sensor module.

9. The method of claim 1, wherein detecting the input operation comprises:
detecting a contact operation including contacting at least a part of a surface of the sensor module; and
detecting a separation operation including being separated from the surface of the sensor module;
and
wherein acquiring the image comprises:
changing a setting of the camera module according to the contact operation; and
acquiring the image through the camera module according to the separation operation.

10. The method of claim 9, wherein detecting the input operation comprises detecting a state in which a contact is maintained after the contact operation; and
wherein acquiring the image comprises waiting for a predetermined time based on a time for which the contact is maintained before the image is acquired.

11. The method of claim 1, further comprising acquiring heart rate information of the subject to be examined based on the input signal.

12. The method of claim 11, further comprising displaying the heart rate information on the image.

13. The method of claim 12, wherein displaying the heart rate information comprises:
identifying the subject to be examined in the image; and
displaying the heart rate information to be associated with the identified subject to be examined.

14. The method of claim 13, wherein displaying the heart rate information to be associated with the identified subject to be examined comprises displaying the heart rate information on a part corresponding to a face or a chest of the subject to be examined.

15. The method of claim 11, further comprising displaying the heart rate information on a preview image acquired through the camera module.

16. The method of claim 11, further comprising storing the image while the image includes the heart rate information.

17. The method of claim 1, wherein the input signal includes an optical signal of an illumination sensor included in the sensor module.

18. The method of claim 1, wherein the input operation is detected based on at least the input signal and whether a button functionally connected to the sensor module is open or shut.

19. An electronic device comprising:
a camera module;
a sensor module that receives an input signal including a physiological signal of a subject to be examined; and
a control module that detects an input operation at least based on the input signal and acquires an image through the camera module according to the input operation.

20. The electronic device of claim 19, wherein the physiological signal includes a Photoplethysmography (PPG) measurement signal.

21. The electronic device of claim 19, wherein the control module detects a contact operation including a contact on at least a part of a surface of the sensor module.

22. The electronic device of claim 19, wherein the input operation is detected based on a signal level or a signal pattern of the physiological signal or another input signal received through the sensor module.

23. The electronic device of claim 19, wherein the control module detects a contact operation including a contact on at least a part of a surface of the sensor module, detects a state in which the contact is maintained for a predetermined time after the contact operation, changes a setting of the camera module according to the contact operation, and acquires the image through the camera module when the predetermined time elapses.

24. The electronic device of claim 23, wherein the control module changes the setting of the camera module by controlling a focus or a white balance of the camera module according to the contact operation.

25. A method comprising:
receiving a physiological signal of a user through a biometric sensor of an electronic device; and
acquiring an image through a camera module of the electronic device at least based on a change in the physiological signal, wherein the acquiring includes acquiring the image through the camera module when the physiological signal is no longer received.

26. The method of claim 25, wherein acquiring the image comprises determining whether the physiological signal changes based on a level or a pattern of the physiological signal.

27. A mobile terminal comprising:
a camera module arranged on a front surface or a rear surface of a body of the mobile terminal;
a sensor module for receiving a physiological signal of a user, the sensor module formed on the front surface or the rear surface of the body; and
a control module for acquiring an image through the camera module at least based on a change in the physiological signal, the control module functionally connected to the camera module and the sensor module, wherein the control module is adapted to acquire the image through the camera module when the physiological signal is no longer received.

28. The mobile terminal of claim 27, wherein the control module determines whether the physiological signal changes based on a level or a pattern of the physiological signal.

29. A non-transitory computer-readable recording medium having a program recorded thereon to perform a method, the method comprising:
- receiving a physiological signal of a user through a biometric sensor of an electronic device; and
- acquiring an image through a camera module of the electronic device at least based on a change in the physiological signal, wherein the acquiring includes acquiring the image through the camera module when the physiological signal is no longer received.

* * * * *